United States Patent [19]

White

[11] 4,361,701

[45] Nov. 30, 1982

[54] NOVEL COMPOUNDS, COMPOSITIONS AND PROCESSES

[75] Inventor: David R. White, Kalamazoo, Mich.

[73] Assignee: The Upjohn Company, Kalamazoo, Mich.

[21] Appl. No.: 20,073

[22] Filed: Mar. 13, 1979

[51] Int. Cl.$^3$ .............................................. C07D 323/04
[52] U.S. Cl. ....................................... 549/361; 549/16; 536/16.8
[58] Field of Search ............... 424/180, 118, 117, 114; 536/12, 17, 18, 180; 260/340.3; 549/16

[56] References Cited

PUBLICATIONS

Rosenbrook, W. et al., Biological Abstracts, vol. 66, 50606, (1978).
Rosenbrook, W. et al., J. Antibiotics, vol. 28, 953, 960 (1975).
Knight, J. et al., J. Antibiotics, vol. 28, 136, (1975).
Lemieux, R. et al., Can. J. Chem., vol. 51, 19, 53 (1973).

*Primary Examiner*—Johnnie R. Brown
*Assistant Examiner*—Blondel Hazel
*Attorney, Agent, or Firm*—Joan Thierstein; Sidney B. Williams, Jr.

[57] ABSTRACT

Anomers and asteric mixtures of novel analogs of spectinomycin. Additionally provides novel intermediates and process for preparing spectinomycin analogs.

42 Claims, No Drawings

NOVEL COMPOUNDS, COMPOSITIONS AND PROCESSES

BACKGROUND OF THE INVENTION

1. Field of the Invention

The invention concerns anomers of certain novel analogs of spectinomycin including asteric mixtures thereof. The invention also includes novel intermediates for making spectinomycin analogs. Methods of making spectinomycin analogs is also within the invention.

2. Description of the Prior Art

Spectinomycin is a known antibiotic having the formula

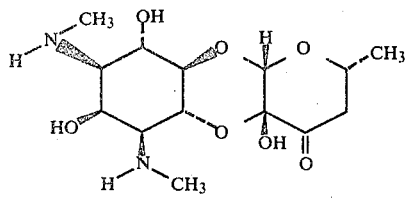

Heretofore, spectinomycin has been prepared by a microbiological process. See Bergy, et al., U.S. Pat. No. 3,234,092. A complete chemical synthesis is now disclosed in copending application Ser. No. 020,172.

Some analogs of spectinomycin are described by Rosenbrook, Jr. et al. in J. Antibiotics, 28, pp. 953 and 960 (1975) and J. Antibiotics, 31, p. 451 (1978). In addition Carney et al. describes chlorodeoxy derivatives of spectinomycin in J. Antibiotics, 30, 960 (1977). Further 9-epi-4(R)-dihydrospectinomycin is reported by Foley et al. in J. Org. Chem., 43, 22 pp. 4355–4359 (1978).

However, contrary to the present invention, biological activity is not reported for any of the spectinomycin analogs and derivatives disclosed in the above cited references.

The prior art disclosing chemical processes nearest the invention process teach a preferential reaction at the 5-hydroxyl of N,N'-dicarbobenzyloxy-2-deoxystreptamine (1) with tri-O-acetyl-2-deoxy-2-nitroso-α-D-glycopyranosyl chloride (2) to give α-pseudodisaccharide (3) in the following manner (see Lemieux, Can. J. Chem. 51, p. 53 (1973)):

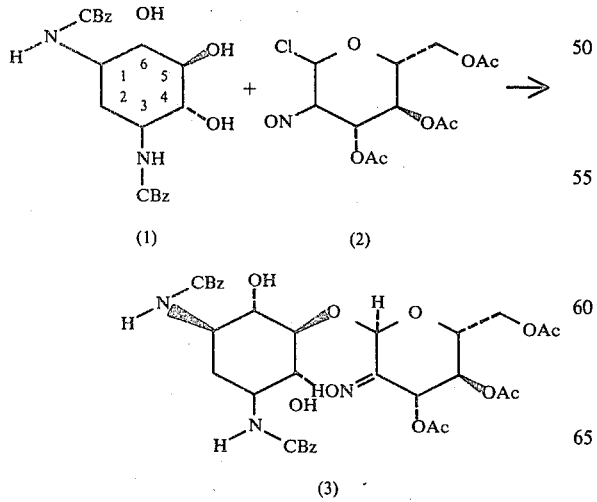

wherein CBz is carbobenzyloxy.

Mallams et al., J. Chem. Soc. Perkin I, p. 1118 (1976), extend the Lemieux reaction to synthesize di- and trisaccharides.

Removal of oximes is taught by Lemieux et al., Can. J. Chem., 51, p. 19 (1973) and Mallams et al., J. Chem. Soc. Perkin I, p. 1097 (1976).

SUMMARY OF THE INVENTION

Compounds of the invention are anomers and asteric mixtures of compounds having the formulae

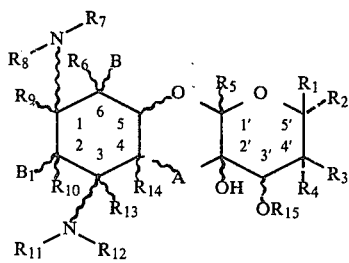

I wherein $R_1$ through $R_4$ may be the same or different and are selected from the group consisting of hydrogen, lower alkyl, lower alkenyl, lower alkynyl, lower haloalkyl, lower aminoalkyl, —OX and —$(CH_2)_n$—OX with the proviso that $R_1$ and $R_2$ are not —OH and when one of $R_3$ and $R_4$ is —OH the other cannot be —OX, wherein X is selected from the group consisting of hydrogen, lower alkyl, lower alkenyl, and lower alkynyl, n is an integer of from one to four, $R_5$–$R_{15}$ are selected from the group consisting of hydrogen, lower alkyl, lower alkenyl and lower alkynyl with the proviso that one of $R_7$ and $R_8$ is always hydrogen and one of $R_{11}$ and $R_{12}$ is always hydrogen, A is oxygen or sulfur, B and $B_1$ are selected from the group consisting of hydrogen, hydroxy, lower alkoxy, —O—lower alkenyl, thiol, thio lower alkyl and thio lower alkenyl with the proviso that when the compound is selected from the group consisting of

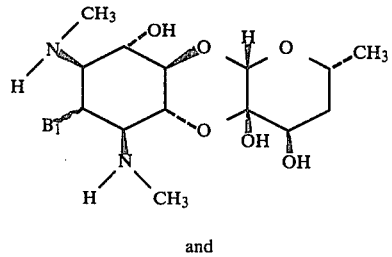

and

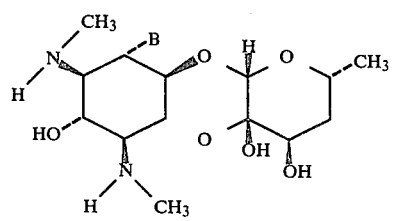

B and $B_1$ cannot be selected from the group consisting of hydrogen and hydroxy, and when the compound is

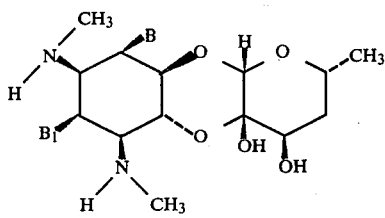

B and $B_1$ cannot both be hydroxy.

The numbering of carbons shown in compound I will be used in discussions thereof throughout the specification.

In the designation of variables herein, the group "—$(CH_2)_n$—" includes straight chain alkyls and isomers thereof.

"Lower alkyl" means methyl, ethyl, propyl, butyl, pentyl, hexyl, heptyl, octyl, and the isomeric forms thereof, "Lower alkenyl" means ethylidene, propylidene, butylidene, pentylidene, hexylidene, heptylidene, octylidene, and the isomeric forms thereof, "Lower alkynyl" means ethynyl, propynyl, butynyl, pentynyl, hexynyl, heptynyl, octynyl and the isomeric forms thereof, "Lower alkoxy" means methoxy, ethoxy, propoxy, butoxy, pentoxy, hexoxy, heptoxy, octoxy and the isomeric forms thereof, "Acyl" means formyl, acetyl, propionyl, butyryl and pentionyl and isomeric forms thereof, "Aralkyl" means benzyl, phenethyl, phenpropyl, phenbutyl, phenpentyl, diphenylmethyl, diphenyloctyl and isomeric forms thereof and fluorenylmethyl, "Halogenated alkoxycarbonyl" means mono-, di-, tri-halomethoxycarbonyl; mono-, di-, tri-haloethoxycarbonyl; mono-, di-, tri-halopropoxycarbonyl; mono-, di-, tri-halobutoxycarbonyl, mono-, di-, tri-halopentoxycarbonyl and isomeric forms thereof.

"Halo" means fluoro, chloro, bromo and iodo,

"Aralkoxycarbonyl" means benzyloxycarbonyl, phenethoxycarbonyl, phenpropoxycarbonyl, phenbutoxycarbonyl, phenpentoxycarbonyl, diphenylmethoxycarbonyl, diphenyloctoxycarbonyl and isomeric forms thereof and fluorenylmethoxy carbonyl.

"Alkyloxy carbonyl" means methoxy carbonyl, ethoxy carbonyl, isopropyloxy carbonyl, tertiary-butyloxy carbonyl, and tertiarypentyloxy carbonyl.

Actinamine or actinamine derivatives include aminocyclitols depicted by formula III hereinafter.

"Lower haloalkyl" means —$(CH_2)_n$—halo and isomeric forms thereof. The group contains one to three halo substituents.

"Lower aminoalkyl" means

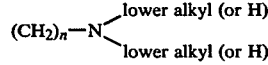

and isomeric forms thereof.

For purposes of this invention an activated sugar starting material as depicted by Formula II hereinafter are derived from substituted pyrans and natural and synthetic sugars, chiral and achiral. Further, it is meant that as used in this description and in the appended claims that when more than one hydroxy or alkoxy is present on the sugar moiety herein they may be the same or different.

This invention also pertains to a chemical process for preparing spectinomycin-like compounds.

Thus, the invention process realizes the importance of the stereochemistry at the glycosidic bond, i.e. 1' position of compounds of Formula I.

The term "α-anomer" means a 1' substituent below the plane of the ring system and the term "β-anomer" means a 1' substituent above the plane of the ring system. Specifically, "β-anomer" means having spectinomycin chirality of C-1'.

Compounds of this invention which exhibit desirable biological activity are β-anomers of compounds of the invention. This glycosidic configuration is found in spectinomycin shown on Page 1. Therefore, adequate selectivity at the 1' position is desirable to obtain biologically active analogs of spectinomycin.

The process of this invention is advantageous in that it provides a chemical synthesis for antibacterial compounds which are analogs of spectinomycin. Heretofore, the prior art has not appreciated the possibility of obtaining a wide variety of spectinomycin analogs in a process which makes a six membered hemiketal of spectinomycin-like structure having biological activity by converting delta hydroxy oximes to delta hydroxy ketones.

An additional advantage of the invention process appears in that an initial actinamine or aminocyclitol reactant having protected amine groups is found to react preferentially at the C-5 hydroxyl without additional protection for other β or α-hydroxyls at the C-2, C-4 or C-6 positions to produce the spectinomycin like configuration. (The numbering of carbons referred to herein is based on that shown in the process scheme in the following paragraph). Thus, surprisingly a difficult and cumbersome protection of hydroxyls not at the C-5 position on the actinamine reactant is unnecessary in the process disclosed herein.

The novel process of this invention can be represented schematically as follows:

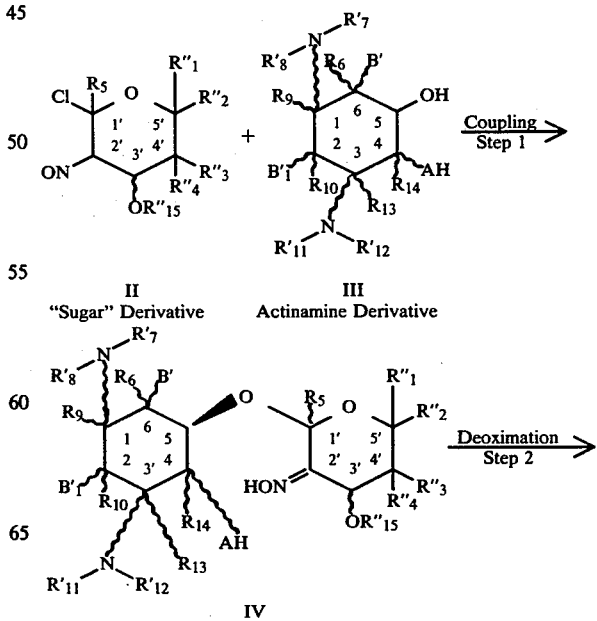

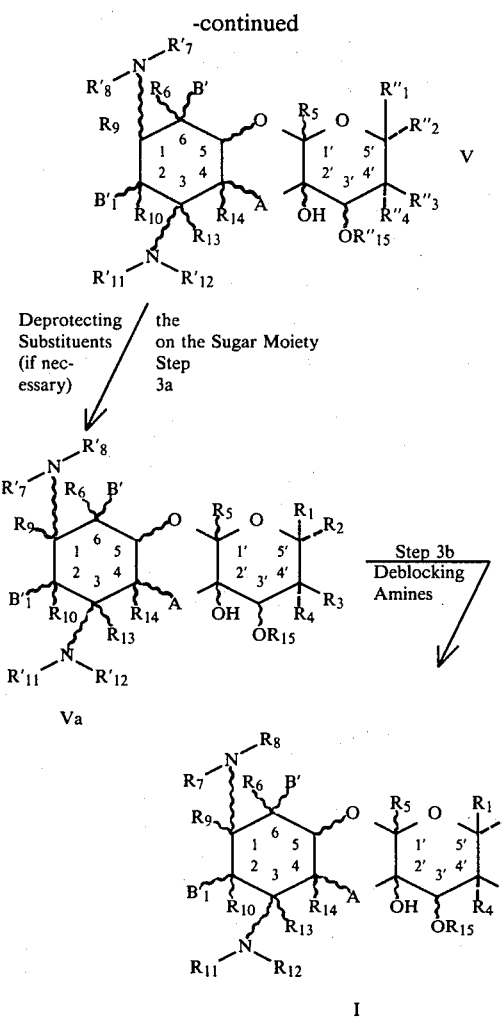

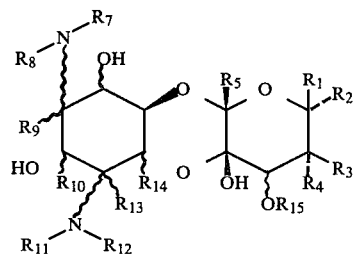

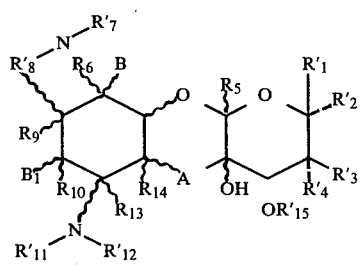

wherein $R_1''$ through $R_4''$ may be the same or different and are selected from the group consisting of hydrogen, lower alkyl, lower alkenyl, lower alkynyl, lower haloalkyl, lower aminoalkyl, —OX″ and —(CH$_2$)$_n$—OX″, wherein X″ is lower alkyl, lower alkenyl, lower alkynyl, acyl and aralkyl, $R_7'$, $R_8'$, $R_{11}'$ and $R_{12}'$ are selected from the group consisting of lower alkyl, lower alkenyl, lower alkynyl and a blocking group selected from the group consisting of carbobenzyloxy, acyl, haloacyl, aralkoxy carbonyl, aryloxycarbonyl, halogenated alkoxycarbonyl and alkyloxy carbonyl with the proviso that one of $R_7'$ and $R_8'$ and one of $R_{11}'$ and $R_{12}'$ is always a blocking group.

$R_{15}''$ is selected from the group consisting of lower alkyl, lower alkenyl, lower alkynyl, acyl and aralkyl, B′ and B$_1'$ are selected from the group consisting of hydrogen, hydroxy, lower alkoxy, -O-lower alkenyl, thiol, thio lower alkyl and thio lower alkenyl, n, $R_5$ through $R_{15}$ and $R_1$ through $R_4$ are as defined for compound I above.

Although both α and β anomers are usually formed in the step 1 coupling reaction of the above process, the β anomers may be preferentially obtained by the separation of β from α anomers following any step in the process. Also the utilization of an available enantiomeric sugar in the initial coupling reaction to give a high proportion of the β anomer, or epimerization of any intermediate or final product may increase the amount of β anomer obtained. Furthermore, asteric mixtures can themselves be utilized as antibacterials in as much as biological activity is present as a consequence of an active anomer therein.

Therefore, "anomers and asteric mixtures of a compound" includes analogs of spectinomycin within the invention having antibacterial activity. Although the β configuration is the active anomer of the invention, the term "anomers and asteric mixtures" is not meant to be limiting since novel α anomers may also be present without detracting from activity in an asteric mixture. Also α anomers of the spectinomycin analog may in some cases be advantageously anomerized to the active form of the analog. Therefore, the α configuration is not excluded at any step in the invention process.

On the other hand, compounds of use in the invention are compounds which have the β configuration because these anomers exhibit antibacterial properties. Separation of these anomers may be accomplished following any step in the process. Preferred β anomers and process of the invention are compounds including C-2 and C-6 hydroxyls having the following formulae:

wherein all substituents are as previously designated.

Another aspect of this invention is novel intermediates in the process.

These intermediates include:

(i) anomers and asteric mixtures of compounds having the formula n, $R_5$–$R_6$, $R_9$–$R_{10}$, $R_{13}$–$R_{14}$, $R_7'$, $R_8'$, $R_{11}'$, $R_{12}'$, A, B, and B$_1$ are as defined above, wherein $R_1'$ through $R_4'$ may be the same or different and are selected from the group consisting of hydrogen, lower alkyl, lower alkenyl, lower alkynyl, lower haloalkyl, lower aminoalkyl, —OX′ and —(CH$_2$)$_n$—OX′ with the proviso that $R_1'$ and $R_2'$ are not OH and when one of $R_3'$ or $R_4'$ is OH the other cannot be OX′, $R_{15}$ is hydrogen, lower alkyl, lower alkenyl, lower alkynyl, acyl and aralkyl, wherein X′ is selected from the group consisting of hydrogen, lower alkyl, lower alkenyl, lower alkynyl, acyl and aralkyl; and (ii) anomers and asteric mixtures of compounds having the formula

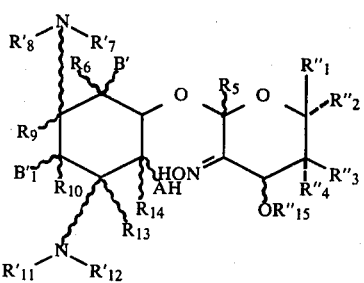

IV n, $R_5$–$R_6$, $R_9$–$R_{10}$, $R_{13}$–$R_{14}$, $R_7'$–$R_8'$, $R_{11}'$–$R_{12}'$, $R_{15}''$, $R_1''$ through $R_4''$, A, B' and $B_1'$ are as defined above, with the proviso that when the compound is

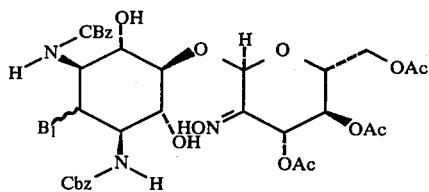

wherein CBz is carbobenzyloxy then $B_1$ cannot be hydrogen.

DETAILED DESCRIPTION OF THE INVENTION

Noval analogs of spectinomycin and intermediates necessary for preparation thereof can be prepared in accordance with the process outlined above. The process is also a generic method to prepare a wide variety of spectinomycin analogs. Spectinomycin is an aminocyclitol antibiotic having a unique structure in that it is a single sugar component fused to an actinamine by both a β-glycosidic bond and a hemiketal bond. The method according to the invention for preparation of the analogs having this unique fusion is a synthesis which couples a sugar derivative and a protected actinamine. The compound prepared by the method may include variations in the actinamine moiety by use of a modified actinamine or aminocyclitol in the synthesis and may include variations in the sugar moiety by use of a modified sugar therein.

The process consists of three basic steps as can be seen by the schematic diagram above. Step 1 selectively couples an active sugar II with the 5-OH of an actinamine III having blocked amine groups. Step 2 deoximates an intermediate IV of step 1 forming a cyclic hemiketal V, which compound also contains the spectinomycin-like β-glycosidic bond of the step 1 coupling.

Step 3 deprotects the sugar portion and the actinamine portion as is made necessary by the use of corresponding protected reactants in step 1.

More particularly, step 1 includes as reactant a sugar or modified sugar, activated in preparation for use by addition of nitrosyl chloride to a double bond in the sugar by known methods as follows:

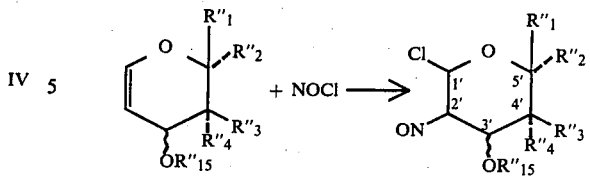

wherein $R_1''$–$R_4''$ and $R_{15}''$ are all defined above. It is significant that, if free hydroxyls are desired on the sugar moiety in the substituents at C3'–C6' positions in the final compound, corresponding groups in the initial sugar reactant are protected by replacement of hydrogen in the hydroxy by acyl or aralkyl groups in a manner known for this purpose in the art. The sugar is commercially available or is known from disclosures, for example, by Mochalin et al., Chem. Het. Comp. 699 (1977) (English translation of KHIM Geterotsiklsoedin, 867 (1977)).

Prior to step 1 the two amino groups of the actinamine derivative are also protected by blocking each with a blocking group such as acyl, aralkoxycarbonyl, haloalkyloxycarbonyl, aralkoxycarbonyl or alkoxycarbonyl groups which are well known in the art for this use. For example, background information on the preparation and removal of carbobenzyloxy and carbo-tert-butyloxy derivatives of amino acids is described by R. A. Boissonas Chapter, "Selectively Removable Amino Protective Group used in the Synthesis of Peptides.," In:Advances in Organic Chemistry, 3:159-190 (1963). Information on the use of the t-butyloxycarbonyl group to block amine is also described in ALDRICH Technical Information Bulletin entitled BOC-OH (September, 1976). Information on the use of trichloroethoxycarbonyl to block amines is disclosed by Windholz, et al., Tetrahedron Letters, 2555 (1967). Finally, an actinamine is available as described in step I for example, from disclosure by Suami, et al. in Tetrahedron Letters, p. 2655 (1968) or in Bull. Chem. Soc. Japan 43, 1843 (1970).

The step 1 coupling reaction occurs in a solution of N,N-dimethyl formamide or similar solvent, such as diethyl ether, tetrahydrofuran or dimethoxymethane sometimes in the presence of a base. The reaction is most efficaciously run under nitrogen atmosphere at ambient temperatures and pressures such as described for a similar reaction by Lemieux, et al., Can. J. Chem. 51, 53 (1973). The temperature range of the reaction is generally 0° C. to 45° C. with molar ratios of activated sugar in solvent of 0.01 M to 0.5 M added to actinamine in solution at a concentration of 0.01 M to 0.5 M such that in a reaction mixture the molar ratio of sugar to actinamine ranges from 1:3 to 3:1. Preferrable reaction conditions are a temperature of 20° C. to 30° C. using dimethylformamide as solvent with the ratio of sugar to actinamine from 3:2 to 2:3. Time of the reaction may range from 4 hours to 1 week but is preferably from 24 hours to 48 hours.

The oxime IV produced is generally isolated from the reaction mixture by concentration or from concentration plus vigorous stirring with an excess of water. The resulting solid is taken up in chloroform and subsequently evaporated to dryness to yield the crude oxime intermediate. α and β anomers may be further separated into fractions by chromatograpghhy on a Silica gel column eluted with methanol in chloroform in the ratio of 1:99 to 2:98. However, use of conventional recovery means such as extraction, crystallization, chromatography and combinations thereof are within the process of the invention.

Step 2 involves removal of the oxime group of compound IV from step 1 to form a cyclic hemiketal, compound V above. The step 2 reaction is conducted by methods for deoximation similar to those described by Lemieux, et al., in Can. J. Chem. 51, 19 (1973) and by Mallams, et al., in J. Chem. Soc. Perkins I 1097 (1976). Products of the literature procedures are ketones, not hemiketals obtained herein.

For example, the deoximation reaction is conducted by dissolving either the crude oxime or the separated α and β oximes of step 1 compound V in a solvent with subsequent addition of acetaldehyde and hydrochloric acid. Initial concentration of oxime in solvent is from 0.01 M to 1.5 M, but preferably 0.1 M to 0.3 M and the molar ratio of the aldehyde to the oxime is from 1:1 to 80:1. 1 N hydrochloric acid is added in about a 2:3 ratio with the oxime. The reaction mixture is stirred at room temperature for from 3.75 hours to 1 day at which time sodium bicarbonate may be added with an additional 15 minutes of stirring. Alternatively, the concentrate may be chromatographed directly such that silica gel removes hydrogen chloride during the purification.

Intermediate V is recovered by conventional means as described above. One suggested recovery is by preparation of a filtrate which is evaporated to dryness in vacuo to yield the crude product. Again this product may be repeatedly fractionated on a silica gel chromatograph using a chloroform-methanol eluant in about a 95:5 ratio. Pooling of similar fractions consistent with thin layer chromatographic analysis thereof and subsequent evaporation to dryness in vacuo yields separate α and β anomers of hemiketal encompassed by structural formula V.

Bases other than sodium bicarbonate can be used in step 2 deoximation, however, maintaining the lack of hydrolytic conditions is critical at this stage to prevent diversion away from the cyclized intermediates which are stable and useful in making analogs within the invention. Therefore, bases used must be those that will not attack acetates i.e. hydroxides cannot be used in excess. Useful examples include benzoates, or hydrogen dipotassium phosphate.

Solvents that may be used include acetonitrile, tetrahydrofuran, ether, or dimethylformamide. The preferred solvent is acetonitrile.

Step 3 removes protective groups on the sugar moiety and deblocks amines on the actinamine of Compound V as shown in the following schematic diagram:

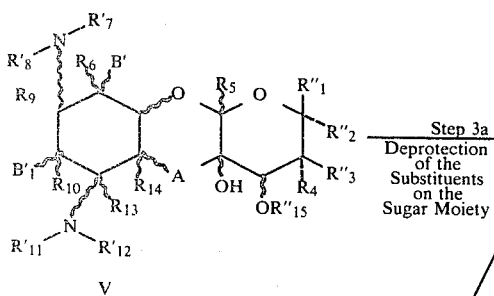

V

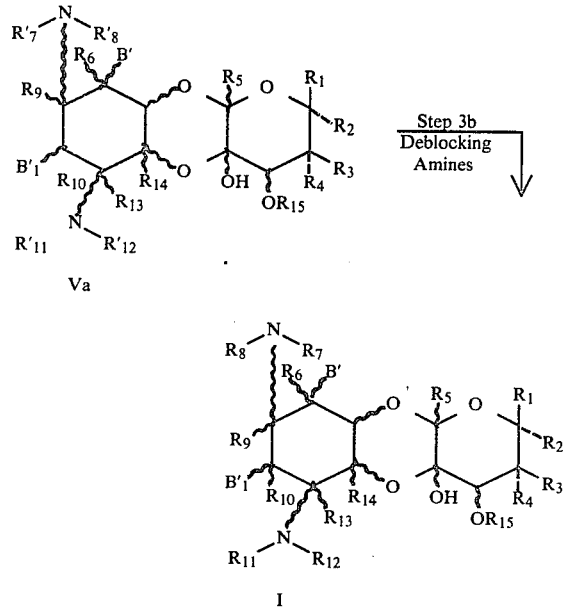

$B'$, $B_1'$, $R_1''-R_4''$, $R_{15}''$, $R_1-R_{15}$, $R_7'-R_8'$ and $R_{11}'-R_{12}'$ are all as defined above.

The way in which removal is accomplished depends upon the particular protective groups on the sugar moiety as well as on the actinamine moiety of intermediate V. In general the protective groups on the sugar moiety are less difficult to remove than those on the actinamine moiety. However, the notation 3a and 3b suggested above is not meant to limit the order of procedures in step 3 since any method to remove protective groups from intermediate V is within the process contemplated herein to obtain Compounds of Formula I.

Although any conventional methods may be used it is suggested that either compounds V are dissolved in methanolic hydrogen chloride and converted intermediates are recovered or compounds V are dissolved in anhydrous methanol to which mixture is added $K_2HPO_4$ in a molar ratio of 50:1 to 1:50 and converted intermediates (Va) are recovered. Recovery is accomplished by any means known in the art. One such means is by concentration in the first suggested conversion and another is by evaporation of a filtrate prepared from the reaction mixture. (The above mentioned methanolic hydrogen chloride is prepared by adding acetylchloride to absolute methanol in a volume ratio of 1:1000 to 1:1). After the mixture is allowed to stand ½ hour to 22 hours it is concentrated. The concentrate is diluted with chloroform followed by the addition of a small excess of trimethylamine. The solution is then concentrated again for use as described above.

On the other hand, if substituents on the sugar moiety of compound V include those desired on the final product of the invention process, no step 3a is necessary. Since in this case intermediate Va is the same as intermediate V, step 3b is appropriate to deprotect the amines thereon directly to a final product I.

The particular conditions of the step 3b deblocking depends upon the particular oxy groups, i.e. group $R_7'$ or $R_8'$ and $R_{11}'$ or $R_{12}'$, that block the amine on the actinamine ring. Where that group is benzyloxy or aralkoxycarbonyl the deprotection can be conducted under from −10 psi to +200 psi of hydrogen over a conventional catalyst such as palladium black, palladium on carbon, palladium on barium sulfate or palladium on barium carbonate, while suspended in a solvent, for example, absolute ethanol, isopropanol, ethyl acetate, toluene or tetrahydrofuran.

Alternatively, deblocking of compounds wherein $R_7'$ or $R_8'$ and $R_{11}'$ or $R_{12}'$ are alkoxycarbonyl or aryloxycarbonyl can be conducted in the presence of an acid in solvents such as nitromethane and methylene chloride.

When $R_7'$ or $R_8'$ and $R_{11}'$ or $R_{12}'$ are haloalkoxycarbonyl, the deblocking is preferably conducted in the presence of zinc.

Any method within the skill in the art may be used for isolation of an analog or asteric mixture of a compound having formula I and suggestions herein are not meant to be limiting. One such suggestion includes evaporation of the excess solvent and formation of a crystalline salt of the compound. These salts may be formed using a solution of an acid such as toluenesulfonic acid, hydrochloric acid, hydrobromic acid, hydroiodic acid, phosphoric acid, acetic, succinic, maleic, fumaric, methanesulfonic, benzenesulfonic, helianthic, Reinecke's azobenzenesulfonic, and picric acid or other acids in a solvent such as water, methanol, ethanol, isopropanol, ether, 1,2-dimethoxyethane or p-dioxane. The salt is isolated by filtration and direct crystallization or by evaporation of the solvent followed by subsequent recrystallization from a suitable solvent.

Alternatively, the crude analogs may be purified by adsorption on to a column of a weakly acidic ion exchange resin such as Amberlite IRC-50 or CB-50 followed by elution with a solvent such as water, methanol, ethanol, ether, tetrahydrofuran, 1,2-dimethoxy ethane or p-dioxane containing hydrogen chloride, hydrogen bromide, hydrogen iodide and sulfuric acid.

Similarly, the salts of hydroxy analogs may be reconverted to the free analog by passing a solution of the salt in solvent such as water, methanol, ethanol, tetrahydrofuran or 1,2-dimethoxy ethane through a basic ion exchange resin such as Dowex 1-X8 (OH-) and evaporating the eluate containing the analogs having free base.

Each step of the above process can be conducted on asteric mixtures of various anomers or on the desired $\beta$ anomer itself obtained by resolution or separation at any stage in the process. The remaining steps may be conducted on $\beta$-intermediates resulting in the desired biologically active anomers.

The preferred method is to separate $\beta$ anomers from the mixture resulting from step 1 coupling of sugar and actinamine and to conduct steps 2 and 3 of the process on the $\beta$ anomers producing only analogs of spectinomycin which are biologically active.

Separation of the anomers from asteric mixtures can be accomplished with modifications obvious to those skilled in the art utilizing conventional methods of resolution. For example, compound IV may be separated so as to obtain a desired $\beta$ component by chromatography on a silica gel column eluted with a mixture of methanol in chloroform in the ratio of 1:99 to 2:98. Likewise, separation of $\beta$ anomers may be effected on an asteric mixture of compound V by pooling $\beta$ fractions obtained on a silica gel chromatograph with a chloroform-methanol eluent. Subsequent evaporation to dryness in vacuo yields a separated hemiketal having the $\beta$ structure.

Another particularly effective method within the invention and therefore preferred is to obtain a relatively high concentration of a $\beta$ anomer in the step 1 coupling reaction by using an enantiomeric sugar favoring formation of the $\beta$ structure. For example, D-arabinose yields $\beta$ and $\alpha$ oximes in an approximately 4:1 ratio. In addition to avoiding costly and time consuming separation procedures on intermediates or resulting products to obtain the $\beta$ configuration the enantiomer may also be available in quantities which are inexpensive. Thus, use of such an enantiomer results in a recovered mixture substantially enriched in the desired $\beta$ anomer which may be brought to purity by the use of a method as described above or may be used without further purification.

Acid salts can be made by neutralizing compounds of formula I with the appropriate acid to below about pH 7.0, and advantageously to about pH 2 to pH 6. Suitable acids for this purpose include hydrochloric, sulfuric, phosphoric, sulfamic, hydrobromic, acetic, succinic, maleic and fumaric, methanesulfonic, benzenesulfonic, helianthic, Reinecke's, azobenzenesulfonic picric acids and the like. Acid and base salts of the compounds can be used for the same biological purposes as the parent compound.

The compounds of formula I inhibit the growth of microorganisms in various environments. For example, formula I compounds having the $\beta$ configuration are active against *Escherichia coli* and can be used to reduce, arrest, and eradicate slime production in papermill systems caused by its antibacterial action against this microorganism. These $\beta$ anomers also can be used to prolong the life of cultures of *Trichomonas foetus, Trichomonas hominis,* and *Trichomonas vaginalis* by freeing them of *Escherichia coli* contamination. Still further, $\beta$ anomers are active against *Bacillus subtilis* so it can be used to minimize or prevent odor in fish or fish crate caused by this organism. Also the anomers can be used to swab laboratory benches and equipment in a mycological laboratory. $\beta$-anomers are also effective against Klebsiella pneumoniae.

The compounds of formula I are also effective for treating bacterial infections; such as gonorrhea in mammals, including humans.

The compositions of the present invention are presented for administration to humans and animals in unit dosage forms, such as tablets, capsules, pills, powders, granules, sterile parenteral solutions or suspensions, eye drops, oral solutions or suspensions, and water-in-oil emulsions containing suitable quantities of the compound of Formula I.

For oral administration, either solid or fluid unit dosage forms can be prepared. For preparing solid compositions such as tablets, the compound of Figure I is mixed with conventional ingredients such as talc, mangesium stearate dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The term "unit dosage form", as used in the specification, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include, for example, the route of administration and the potency of the particular compound. A dosage schedule for humans of from about 2 to about 4000 mg. of compound in a single dose, administered parenterally or in the compositions of this invention, are effective for treating bacterial infections. More specifically, the single dose is from about 5 mg. to about 2000 mg. of compound. The oral and rectal dose is from about 5 mg. to about 3500 mg. in a single dose. More specifically, the single dose is from about 10 mg. to about 2500 mg. of compound.

The following described preparations of analogs of spectinomycin and intermediates useful in the preparation thereof are indicative of the scope of this invention and are not to be construed as limitative. Those skilled in the art will promptly recognize variations from the procedures both in the analogs and analog precursors within the novel compounds described as well as reaction conditions and techniques of the invention process.

For example, for each of the Preparations and Examples in the following descriptions, corresponding stereoisomers for each named compound is contemplated to be within the scope of the invention.

PREPARATION OF ANALOGS OF SPECTINOMYCIN

Preparation 1

5-O-(3',4',6'-Tri-O-acetyl-2'-oximino-2'-deoxy-β-D-gluco-pyranosyl)-N,N'-dicarbobenzyloxyactinamine.

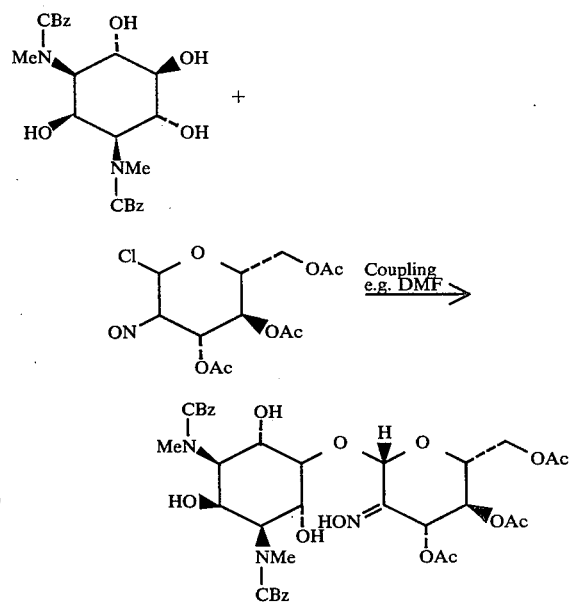

A solution of 8.4 g. (24 mmol) of 3,4,6-tri-O-acetyl-2-nitroso-2-deoxy-α-D-glucopyranosyl chloride and 11.4 g. (24 mmol) of N,N'-dicarbobenzyloxyactinamine in 180 ml. of N,N-dimethylformamide (DMF) is stirred at room temperature for two days. The solvent is removed by distillation under reduced pressure at approximately 50° C. The residue is chromatographed on 1.5 kg of silica gel collecting 20-ml fractions. After 150 fractions using CHCl$_3$-CH$_3$OH (99:1) as eluant the solvent is changed to CHCl$_3$—CH$_3$OH (98:2) and 850 more fractions are collected. The fractions are analyzed by TLC (CHCl$_3$=CH$_3$OH 95:5) and the second group of fractions (714–747) giving only one spot is combined. The pool is evaporated to dryness in vacuo to give 0.5 g. (2.5%) of β-oxime PMR (CDCl₃) δ2.04

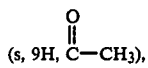

δ3.05 (s, 6H, N-CH₃), δ3.3-4.6 (m, 10H, OCH, NCH), δ5.13 (s, 4H, C₆H₅CH₂O), δ5.5 (d, 1H, C-3′, J=4 H₂), δ5.74 (s, 1H, anomeric), δ7.32 (s, 10H, phenyl); CMR (d₆-CH₃COCH₃) 170.7, 169.8, 169.4 (3CH₃CO), 157.6, 156.9 (OCON), 150.3 (C=NOH) 138.1 (C-1 of phenyl), 129.1, 128.3 (C-2 thru C-6 of phenyl), 96.0 (C-1′), 91.9 (C-5 or C-5′), 73.6, 70.5, 70.1, 67.7, 64.1, 60.5, 60.1, 59.7, 59.5 (C-O and C-N), 67.3 (φCH₂O), 31.7 (2CH₃N), 20.8, 20.6 (3CH₃CO); Mass spectrum m/e [4(CH₃)₃Si]1063.

Preparation 1a

5-O-(3′,4′,6′-Tri-O-acetyl-2′-oximino-2′-deoxy-α-D-gluco-pyranosyl)N,N′-dicarbobenzyloxyactinamine

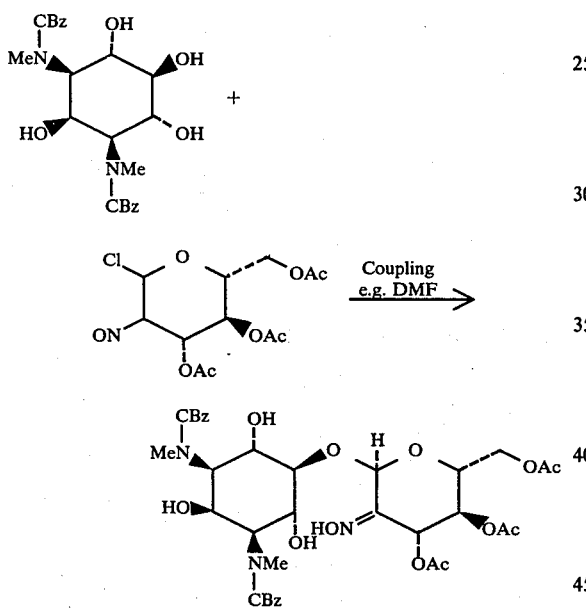

A solution of 3,4,6-tri-O-acetyl-2-nitroso-2-deoxy-α-D-gluco-pyranosyl chloride (28.36 g, 83 mmol) and N,N′-dicarbobenzyloxyactinamine (48.56 g, 102 mmol) is stirred for 24 hours at which time none of the pyranosyl chloride remains. The solution is concentrated at 45° C. and the residue dissolved in chloroform (150 ml) containing 1.5% methanol. This is placed on a 7 l. column of wet packed silica gel. The column is eluted with solvent (1.5% methanol in chloroform). After ~22 l. of solvent are used, a small amount of β product are recovered (1.00 g) followed by fractions containing α and β (0.92 g). At this time, pure α product (23.12 g, 36%) came off of the column. All product fractions are treated with anhydrous trimethyl amine (0.05 ml/ml of solvent) as soon as possible after elution. The fractions are then pooled and concentrated at 40°-50° after treating with trimethyl amine.

Detailed Elution Schedule for 3′,4′,6′-Tri-O-acetyl-2′-oximino-2′-deoxy-α-D-glyco-pyranosyl-N,N′-dicarbobenzyloxyactinamine.

| Total Volume of Solvent | Weight | Product | % CH₃OH in CHCl₃ |
|---|---|---|---|
| 23.5 l to 24.9 l | 1.00 g | β-Anomer | 1½% |
| 24.9 l to 25.9 l | .92 g | α + β | 1½% |
| 25.9 l to 27.7 l | 2.10 g | α ⎫ 36 Yield | 1½% |
| 27.7 l to 36.8 l | 20.92 g | α ⎭ | Change to 4% |
| 36.8 l to 39.2 l | 1.94 g | α-Plus Side | 4% |
| 39.2 l to 48.0 l | 9.27 g | Side Product | 4% |

CD (CH₃OH) [θ]₂₂₆$^{max}$ mμ=18,600±1,300. PMR (CDCl₃): 2.02 (9H, s), 3.03 (6H, s), 5.08 (4H, s), 6.20 (1H, s), 7.32 δ (10H, s). CMR (CD₃COCD₃): 170.8, 170.0, 169.8, 157.7, 157.0, 149.3, 137.9, 129.1, 128.3, 92.1, 85.9, 74.4, 70.4, 69.8, 69.3, 68.6, 67.3, 62.5, 60.6, 31.4, 31.1, 20.6 ppm. Mass spectrum, m/e (tetrasilyl): 1063 (M+), 1048 (M-15), 929, 928, 792, 689, 673, 645, 600, 342.

Preparation 2

5-O-(3′,4′-di-O-acetyl-2′-deoxy-2′-oximino-D-arabinopyranosyl)-N,N′-dicarbobenzyloxyactinamine

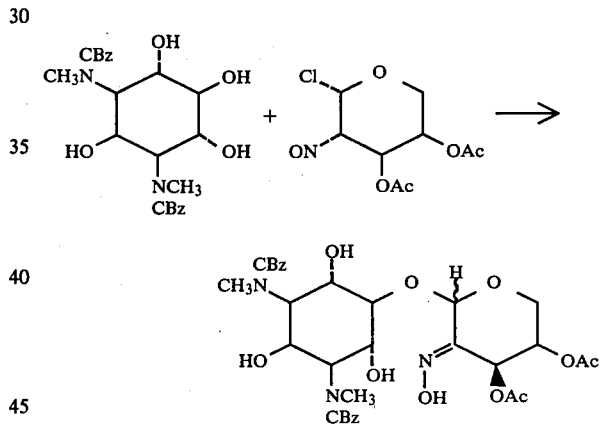

To a solution of 7.20 g (27.10 mmol) of 3,4-di-O-acetyl-2-deoxy-2-nitroso-β-D-arabinopyranosyl chloride in 75 ml of dimethylformamide is added a solution of 11.86 g (25.0 mmol) of N,N′-bis-carbobenzyloxyactinamine in 50 ml of dimethylformamide. The reaction mixture is stirred 19.5 hours at room temperature under a nitrogen atmosphere. The mixture is poured into 1 liter of water with vigorous stirring. The aqueous phase is decanted and the solid is taken up in 300 ml of CHCl₃, the small amount of water is separated and solvent is removed in vacuo to give 12.6 g of a brittle white foam. The total aqueous phase is extracted three times with 100 ml portions of trichloromethane. The combined organics are washed with water and brine (50 ml each) and dried over sodium sulfate. The solvent is reduced to ~40 ml and this solution is added to 300 ml of water with stirring. The small trichloromethane layer is separated and solvent is removed in vacuo to give 6.18 g of white foam which is combined with the other portion. Analysis of the crude product by PMR shows that most of the DMF has been removed by this procedure.

Chromatography on 1.25 kg of silica gel (methanol trichloromethane gradient) affords 1.33 g (1.89 mmol, 7.6%) of the pure α-anomer, followed by 2.86 g (4.06 mmol, 16.3%) of a pure β-anomer (4β) and 3.17 g of β-anomer of ~90% purity. Further elution gives a variety of unsymmetrically glycosylated actinamines (identified as unsymmetrical adducts by periodate reactivity) and recovers N,N'-bis-CBz-actinamine.

For the α-anomer:
IR (CHCl₃) 3550, 3400, 3070, 2980, 1745, 1686, 1675 (sh), 1484, 1449, 1364, 1333, 1235, 1167, 1026, 669 cm⁻¹; PMR (CDCl₃) δ7.40 (s, 10, aromatic) 6.07 (s, 1, H₁'), 5.95 (d, J=3 Hz, 1, H₃') 5.20 (m, 7), 3.3–4.6 (m, 10), 3.12 and 3.08 (s's, 6, NCH₃), 2.12 and 2.03 (s's, 6, CH₃); MS (for tetra trimethylsilyl derivative) 991 (M⁺), 689, 673; CMR (d₆-acetone) δ170.1, 169.8, 157.8, 156.5, 150.1, 138.1, 129.1, 128.8, 128.4, 91.7, 86.9, 79.1, 74.4, 69.1, 68.6, 68.3, 67.8, 67.3, 60.3, 57.7, 31.5, 31.4, 20.8, 20.5; mp 130°–140°, decomposition. High resolution MS (tetra TMS) C₄₅H₇₃N₃O₁₄Si₄ requires 991.4169; found: 991.4190.

For the β-anomer:
IR (CHCl₃) 3500, 3100, 2970, 1748, 1686, 1672, (sh), 1486, 1449, 1370, 1337, 1235, 1167, 1107, 1024, 700 cm⁻¹; PMR (CDCl₃) δ7.40 (s, 10, aromatic), 6.40 (s, 1, H₁') 6.05 (d, 5=3 Hz, 1, H₃'), 5.0–5.5 (m, 6), 3.4—3.8 (m, 11), 3.07 and 3.04 (s's, 6, NCH₃), 2.08, 2.05 (s's, 6, CH₃); MS (for tetratrimethylsilyl derivative), 991 (M⁺), 900, 976, 975, 689, 673; CMR (d₆-acetone) δ 170.7, 169.9, 157.7, 157.1, 149.1, 137.9, 129.1, 128.7, 128.3, 92.3, 85.3, 74.7, 70.8, 69.4, 67.3, 62.0, 60.2, 31.4, 20.8, 20.5; m.p. 140°–155° decomposition. High resolution MS (tetra TMS) C₄₅H₇₃N₃O₁₄Si₄ requires 991.4169; found 991.4229.

Preparation 3

5-O-(4',6'-di-O-acetyl-3'-O-methyl-2'-deoxy-2'-oximino-β-D-glucopyranosyl)-N,N'-dicarbobenzyloxyactinamine

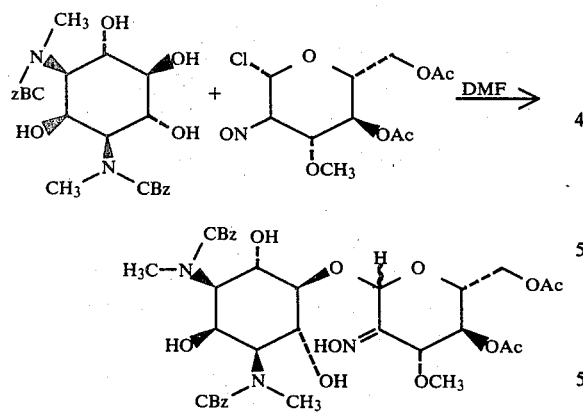

To a solution of 60.8 g (196 moles) of 4,6-Di-O-acetyl-3-O-methyl-2-nitroso-α-D-glucopyranosyl chloride in 1.1 l of DMF is added 97.7 g. (206 mmol) of N,N'-bis-carbobenzyloxyactinamine. Reaction is stirred for 45 hours at room temperature under a nitrogen atmosphere and then concentrated at 30° C. under high vacuum to give a thick syrup. This is poured in portions into a total of 3 liters of chilled water and vigorously stirred. The resulting white solid is filtered off, redissolved in 3 liters of chloroform, separated from the residual water and dried over Na₂SO₄. Concentration of CHCl₃ layer gives 143 g of a sticky white foam containing approximately 7% DMF by NMR integral ratio. Chromatography on 3.5 kg of silica gel using MeOH CHCl₃ gradient elution system gives a rough separation of products. Fractions containing the β-oxime are crystallized from acetone to give 4.4 g of the pure β-isomer. Chromatography of the mother liquors gives 1.5 g of β-isomer.

For the β-oxime:
(IR) 3500, 3310, 2920, 1750, 1690, 1459, 1240, 1175 1105, 1403, 735, 711 cm⁻¹
PMR: (CDCl₃) 7.32 s, 5.41 s, 5.11 s, 3.5–4.5 m, 3.335, 3.045, 2.02
CMR: (CDCl₃) 170.6, 169.6, 157.7, 156.5, 150.1, 136.5, 128.5, 127.8, 95.7, 92.7, 77.1, 73.2, 70.1, 67.54, 64.09, 56.8, 29.7, 20.8, 20.5
Mass spec. (tetra-trimethylsilyl derivative M⁺ 1035 m.p. 214°–216°.

Preparation 3a

5-O-(3',4',6'-Tri-O-acetyl-2'-oximino-2'-deoxy-α-L-glucopyranosyl) N,N'-dicarbobenzyloxyactinamine (3)

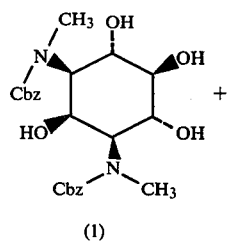

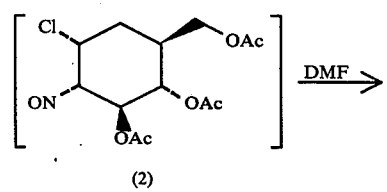

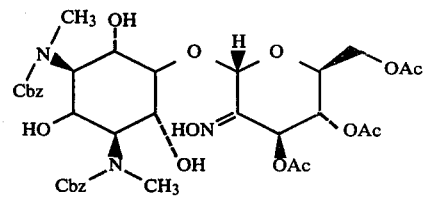

A solution of 3',4',6'-tri-O-acetyl-2'-nitroso-2'-deoxy-α-L-glucopyranosyl chloride (2) (7.09 g, 21 mmol) and N,N-dicarbobenzyloxyactinamine (1) (14.22 g, 30 mmole) in dimethylformamide is stirred for 19 hours at which time none of the pyranosyl chloride (2) remained. The solution is concentrated at 45° and the residue dissolved in chloroform containing 1.5% methanol. This is placed on a column of wet packed silica gel (3 kg.). The column is eluted with solvent (1.5% methanol in chloroform). After about 10 l. of solvent are used, the main product (3) is eluted as judged by TLC (5% methanol in chloroform). The fractions containing pure (3) are combined and concentrated. Yield 7.86 g. (48%).
CD (CH₃OH) [θ]₃₂₆ mμ^max +18,900±1,300.
[α]_D^27 −53° (C 0.9, acetone).
PMR (CDCl₃): 2.02 (9H, s), 3.03 (6H, s), 5.04 (4H, s), 6.20 (1H, s), 7.32 8 (10H, s).

CMR (CD₃COCD₃): 170.8, 170.0, 169.8, 157.7, 157.0, 149.5, 137.9, 129.1, 128.7, 128.3, 92.0, 85.8, 74.4, 70.4, 69.8, 69.4, 68.6, 67.3, 62.5, 60.6, 60.2, 31.4, 31.1, 20.6 ppm.

Mass spectrum, m/e (tetra TMS): 1063 (M+), 1048, 793, 792, 689, 674, 645.

Utilizing a procedure similar to Preparations above but substituting the appropriately-substituted actinamine and sugar reactants, there are obtained asteric mixtures from which α and β-anomers may subsequently be obtained as also shown by the procedure in the above Preparations. Table I consists of oximes of such coupling reactions.

TABLE I

| B | B₁ | R"₁ | R"₂ | R"₃ | R"₄ | R"₁₅ |
|---|---|---|---|---|---|---|
| HO— | HO— | H— | CH₃COCH₂— (O) | CH₃CO— (O) | H— | CH₃C— (O) |
| CH₃O— | HO— | " | " | " | " | " |
| C₂H₅O— | HO— | " | " | " | " | " |
| HS— | HO— | " | " | " | " | " |
| CH₃S— | HO— | " | " | " | " | " |
| C₂H₅S— | HO— | " | " | " | " | " |
| H— | HO— | " | " | " | " | " |
| HO— | H— | " | " | " | " | " |
| HO— | CH₃O— | " | " | " | " | " |
| HO— | HO— | " | —CH₂Cl | " | " | " |
| HO— | HO— | " | —CH₂Br | " | " | " |
| HO— | HS— | " | CH₃COCH₂— (O) | " | " | " |
| HO— | CH₃S— | " | " | " | " | " |
| HO— | C₂H₃S— | " | " | " | " | " |
| HO— | HO— | " | (C₆H₅)CH₂OCH₂— | (C₆H₅)CH₂O— | H— | (C₆H₅)CH₂— |
| HO— | HO— | " | (C₆H₅)CH₂O— | " | " | " |
| HO— | " | " | CH₃O— | CH₃C—O— (O) | " | CH₃C— (O) |
| HO— | " | " | C₂H₅— | H— | " | " |
| HO— | " | " | CH₃C—OCH₂— (O) | CH₃C—O— (O) | CH₃OCH₂— | " |
| HO— | " | " | " | " | C₂H₅— | " |
| HO— | " | CH₃OCH₂— | H— | " | H— | " |
| HO— | " | (C₆H₅)CH₂OCH₂— | " | " | " | (C₆H₅)CH₂— |
| HO— | " | H— | —CH₂OC(C₆H₅)₃ | CH₃CO— (O) | " | CH₃C— (O) |
| HO— | " | " | " | —OCH₃ | " | CH₃— |
| HO— | " | " | CH₃C—OCH₂— (O) | H— | H— | CH₃CO— (O) | CH₃C— (O) |
| HO— | " | " | " | CH₃O— | H— | CH₃— |

TABLE I-continued

| B | $B_1$ | $R''_1$ | $R''_2$ | $R''_3$ | $R''_4$ | $R''_{15}$ |
|---|---|---|---|---|---|---|
| HO— | " | " | $CH_3OCH_2$— | $CH_3\overset{O}{\underset{\|}{C}}$—O— | H— | $CH_3$—$\overset{O}{\underset{\|}{C}}$— |
| HO— | " | " | " | $CH_3O$— | " | $CH_3$— |

TABLE II

| B | $B_1$ | $R''_1$ | $R''_2$ | $R''_3$ | $R''_4$ | $R''_{15}$ |
|---|---|---|---|---|---|---|
| HO— | HO— | H— | $CH_3\overset{O}{\underset{\|}{C}}OCH_2$— | $CH_3\overset{O}{\underset{\|}{C}}O$— | H— | $CH_3\overset{O}{\underset{\|}{C}}$— |
| $CH_3O$— | " | " | " | " | " | " |
| $C_2H_5O$— | " | " | " | " | " | " |
| HS— | " | " | " | " | " | " |
| $CH_3S$— | " | " | " | " | " | " |
| $C_2H_5S$— | " | " | " | " | " | " |
| H— | " | " | " | " | " | " |
| HO— | H— | " | " | " | " | " |
| HO— | $CH_3O$— | " | " | " | " | " |
| HO— | HO— | " | —$CH_2Cl$ | " | " | " |
| HO— | " | " | —$CH_2Br$ | " | " | " |
| HO— | HS— | " | $CH_3\overset{O}{\underset{\|}{C}}OCH_2$— | " | " | " |
| HO— | $CH_3S$— | " | " | " | " | " |
| HO— | $C_2H_5S$— | " | " | " | " | " |
| HO— | HO— | " | $C_6H_5CH_2OCH_2$— | $C_6H_5CH_2O$— | " | $C_6H_5CH_2$— |
| HO— | " | " | $C_6H_5CH_2O$— | " | " | " |
| HO— | " | " | $CH_3O$— | $CH_3\overset{O}{\underset{\|}{C}}$—O— | " | $CH_3\overset{O}{\underset{\|}{C}}$— |
| HO— | " | " | $C_2H_5$— | H— | " | " |
| HO— | " | " | $CH_3\overset{O}{\underset{\|}{C}}$—$OCH_2$— | $CH_3\overset{O}{\underset{\|}{C}}$—O— | $CH_3OCH_2$— | " |
| HO— | " | " | " | " | $C_2H_5$— | " |
| HO— | " | $CH_3OCH_2$— | H— | " | H— | " |
| HO— | " | $C_6H_5CH_2OCH_2$— | " | " | " | $C_6H_5CH_2$— |
| HO— | " | H— | —$CH_2OC(C_6H_5)_3$ | $CH_3\overset{O}{\underset{\|}{C}}O$— | " | $CH_3\overset{O}{\underset{\|}{C}}$— |
| HO— | " | " | " | —$OCH_3$ | " | $CH_3$— |

TABLE II-continued

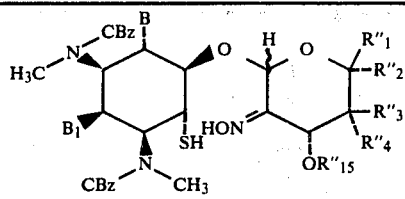

| B | B₁ | R"₁ | R"₂ | R"₃ | R"₄ | R"₁₅ |
|---|---|---|---|---|---|---|
| HO— | " | $\underset{\text{O}}{\overset{\text{O}}{\text{CH}_3\text{C}-\text{OCH}_2-}}$ | H— | H— | $\underset{\text{O}}{\overset{\text{O}}{\text{CH}_3\text{CO}-}}$ | $\underset{\text{O}}{\overset{\text{O}}{\text{CH}_3\text{C}-}}$ |
| HO— | " | " | " | CH₃O— | H | CH₃— |
| HO— | " | " | CH₃OCH₂— | $\underset{\text{O}}{\overset{\text{O}}{\text{CH}_3\text{C}-\text{O}-}}$ | H— | $\underset{\text{O}}{\overset{\text{O}}{\text{CH}_3\text{C}-}}$ |
| HO— | " | " | " | CH₃O— | " | CH₃— |

Although subsequent deoximation reactions and deblocking "oxy" and amine moieties may be accomplished on asteric mixtures or α-anomer fractions, the β fractions from each of the above coupling reactions are separated and used hereafter for the purpose of obtaining the biologically active spectinomycin analogs of the invention.

Preparations 4

N,N'-Dicarbobenzyloxy-3'-O-acetyl-4'-(R)-acetoxy-6'-acetoxy-3'-(S)-dihydrospectinomycin

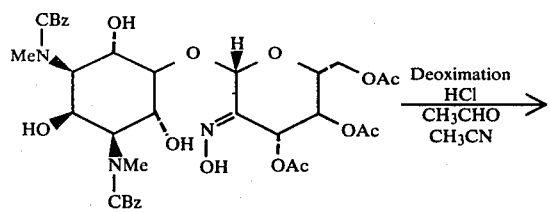

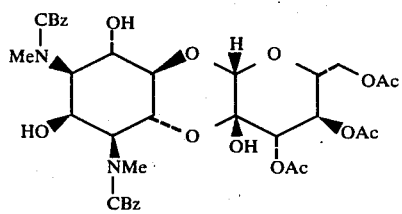

To a solution of 0.77 g (1 mmol) of β-oxime from Preparation 1 in 8 ml of acetonitrile is added 2 ml (36 mmol) of acetaldehyde and 0.8 ml (0.8 mmol) of 1.0 N HCl solution. The mixture is stirred at room temperature for a day at which time 0.26 g (3 mmol) of sodium bicarbonate is added. The mixture is stirred for an additional 15 minutes, filtered and the filter cake is washed with a small amount of acetonitrile. The filtrate is evaporated to dryness in vacuo. The crude product is chromatographed by HPLC using Merck size B pre-packed column and CHCl₃— CH₃OH (99:1) as the eluant. A total of three hundred 5-10 ml fractions are collected. The fractions are analyzed by TLC (CHCl₃-CH₃OH-95:5) and the third group of fractions (160-300) giving only one spot material is combined. The pool is evaporated to dryness in vacuo to give 0.2 g (26%) of the title compound. CMR (d₆-CH₃COCH₃) 170.8, 170.1, 171.3 (3CH₃CO), 157.8, 157.0 (OCON), 138.3 (C-1 of phenyl), 129.2, 128.4, 128.3 (C-2 thru C-6 of phenyl), 95.8, 92.7, 76.0, 75.1, 72.6, 68.6, 66.5, 65.3, 63.4, 60.9, 57.5 (C-O and C-N), 67.3 ($\phi$CH₂O), 31.8 2CH₃N), 20.7 (3CH₃CO); Mass spectrum m/e [3(CH₃)₃Si]976; high resolution mass spectrum called for C₄₅H₆₈O₁₆Si₃: 976.38765. Found 976.38784.

Preparation 4a

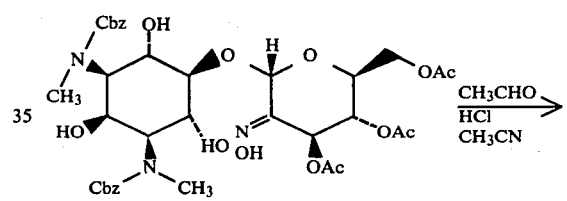

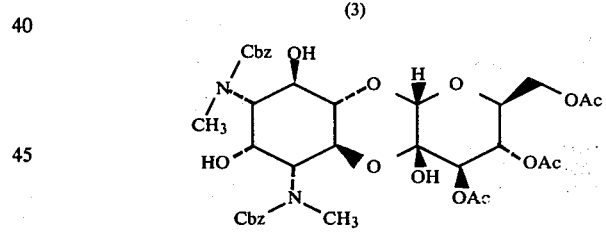

A solution of (3) (7.00 g., 9.03 mmole) from Preparation 3a, and acetonitrile (70 ml.), acetaldehyde (14.2 ml.) and 1 N aqueous HCL (2 ml.) is stirred at room temperature for about 5 hours. Anhydrous sodium sulfate (60 ml.) is added and stirred for 10 minutes. The solid is filtered and washed with acetonitrile. The filtrate is concentrated, taken up in chloroform-ethylacetate (1:1) (15 ml.) and chromatographed on silica gel (150 g.) using the same solvent. The eluate is evaluated by TLC (5% methanol in chloroform) and pure fractions are combined and concentrated to give 5.96 g (87%) of hemiketal triacetate (4).

[α]$_D^{27}$ —52° (C 0.7, chloroform).

PMR (CDCl₃): 2.06 (9H, s), 2.88 (3H, s), 4.90 (s), 5.13 (4H, s), 7.38 δ(10H, s).

CMR (CD₃COCD₃): 170.1, 169.4, 137.5, 137.4, 128.6, 127.9, 99.2, 94.0, 82.2, 73,9, 70.6, 68.4, 68.0, 66.8, 65.6, 62.3, 60.4, 57.3, 30.0, 20.0.

Mass spectrum (tri TMS): m/e 976 (M+), 961 (M+−15), 917, 841, 705, 552.

This compound can be converted to an active compound. Methods for said conversion to natural configuration can be found in copending U.S. application Ser. No. 020,172, filed Mar. 13, 1979, abandoned, continuation of U.S. Pat. No. 4,351,771, May 16, 1980, pending Ser. No. 359.006, Mar. 17, 1982.

Preparation 5

N,N'-dicarbobenzyloxy-3'-O-acetyl-4'-(R)-acetoxy-5'-demethyl-3'-(R)-dihydrospectinomycin

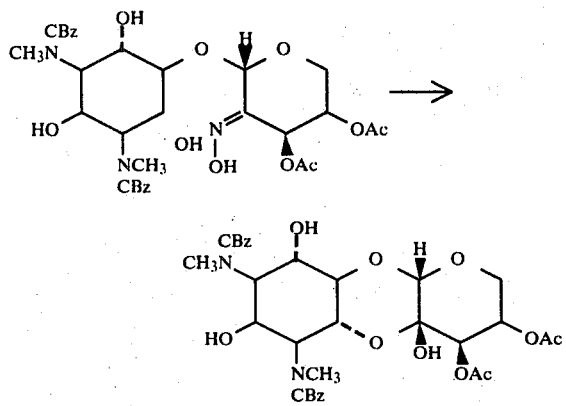

The β-oxime from Preparation 2 (2.32 g, 3.30 mmol) is dissolved in 30 ml of CH₃CN and 5.0 ml (89.4 mmol) of acetaldehyde and 2.5 ml (2.50 mmol) of 1 N HCl are added. The reaction mixture is stirred 3.75 hours at room temperature. Na₂SO₄ is added and stirring is continued for 15 minutes. The mixture is filtered and solvent is removed in vacuo to afford 2.6 g of white solid. Chromatography on 200 g of silica gel (CH₃OH/CHCl₃ gradient) gives 1.45 g (2.11 mmol, 64%) of N,N'-dicarbobenzyloxy-3'-O-acetyl-4'-(R)-acetoxy-5'-demethyl-3'-(R)-dihydrospectinomycin as a white solid: m.p. 135.0°–142.9°; IR (CHCl₃) 3450, 3050, 1748, 1684, 1481, 1447, 1362, 1333, 1238, 1160, 1050, 1020, 680 cm⁻¹; PMR (CDCl₃) δ7.4 (s, 10, aromatic), 3.4–5.4 (m), 3.05 (s, 6, NCH₃), 2.10 (s, 3, COCH₃), 1.95 (s, 3, COCH₃); CMR (d₆-acetone) δ170.2, 169.8, 157.5, 156.9, 138.0, 129.1, 128.3, 94.6, 91.5, 74.7, 72.4, 67.3, 67.0, 66.3, 65.6, 61.7, 61.2, 57.5, 31.6, 20.6; MS (for tris-trimethylsilyl derivative) 904 (M+).

Preparation 6

N,N'-dicarbobenzyloxy-3'-O-methyl-4'-(R)-acetoxy-6'-acetoxy-3'-(S)-dihydrospectinomycin

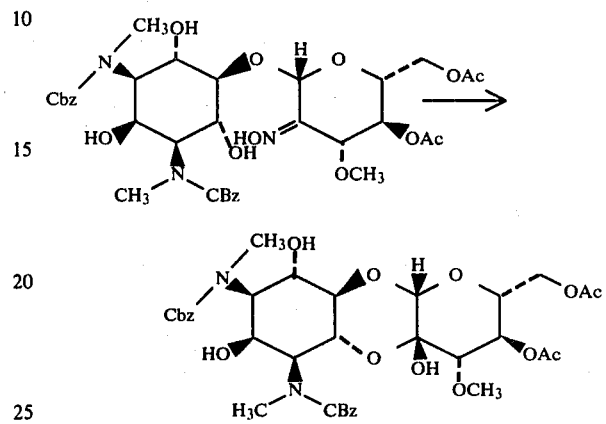

To a suspension of β-oxime from Preparation 3, 300 mg (0.40 mmol) in 12 ml of acetonitrile is added acetaldehyde 12 ml and HCl 0.18 ml (1.0 N) and stirred for 60 hours. The homogeneous solution was stirred with Na₂SO₄ for 20 minutes and filtered. Chromatography of the crude product on 10 g of silica gel in 15% trichloromethane-ethylacetate gave 150 mg. of product.

PMR (CDCl₃) 7.32, 5.1 s, 4.68 s, 3.5 s, 3.1, 2.1

CMR (d₆-acetone) 171.0, 170.3, 157.8, 138.2, 128.2, 128.5, 95.8 93.8, 84.5, 75.2, 73.1, 69.8, 67.4, 66.4, 65.2, 63.7, 61.2, 57.9, 57.5, 30.8, 29.8, 21.0, 20.7.

Mass spec. (tri-trimethylsilyl derivative) (M+)948 (M-15) 933.

Using the procedure of Preparations 4, 4a, 5, or 6 but substituting the appropriately-substituted precursor oxime from Tables I and II there is obtained a spectinomycin analog having protecting groups as follows:

TABLE III

| B | B₁ | R"₁ | R"₂ | R"₃ | R"₄ | R"₁₅ |
|---|---|---|---|---|---|---|
| HO— | HO— | H— | CH₃COCH₂— (O=) | CH₃CO— (O=) | H— | CH₃C— (O=) |
| CH₃O— | HO— | " | " | " | " | " |
| C₂H₅O— | HO— | " | " | " | " | " |
| HS— | HO— | " | " | " | " | " |
| CH₃S— | HO— | " | " | " | " | " |
| C₂H₅S— | HO— | " | " | " | " | " |
| H— | HO— | " | " | " | " | " |
| HO— | H— | " | " | " | " | " |
| HO— | CH₃O— | " | " | " | " | " |
| HO— | HO— | " | —CH₂Cl | " | " | " |
| HO— | HO— | " | —CH₂Br | " | " | " |

TABLE III-continued

| B | B₁ | R″₁ | R″₂ | R″₃ | R″₄ | R″₁₅ |
|---|---|---|---|---|---|---|
| HO— | HS— | H— | CH₃COCH₂— (C=O) | CH₃CO— (C=O) | H— | CH₃C— (C=O) |
| HO— | CH₃S— | " | " | " | " | " |
| HO— | C₂H₅S— | " | " | " | " | " |
| HO— | HO— | " | C₆H₅CH₂OCH₂— | C₆H₅CH₂O— | H— | C₆H₅CH₂— |
| HO— | HO— | " | C₆H₅CH₂O— | " | " | " |
| HO— | " | " | CH₃O— | CH₃C(=O)—O— | " | CH₃C(=O)— |
| HO— | " | " | C₂H₅— | H— | " | " |
| HO— | HO— | H— | CH₃C(=O)—OCH₂— | CH₃C(=O)—O— | CH₃OCH₂— | " |
| HO— | " | " | " | " | C₂H₅— | " |
| HO— | " | CH₃OCH₂— | H— | " | H— | " |
| HO— | " | " | C₆H₅CH₂OCH₂— | " | " | C₆H₅CH₂— |
| HO— | " | H— | —CH₂OC(C₆H₅)₃ | CH₃CO— (C=O) | " | CH₃C— (C=O) |
| HO— | " | " | " | —OCH₃ | " | CH₃— |
| HO— | " | CH₃C(=O)—OCH₂— | H— | H— | CH₃CO— (C=O) | CH₃C— (C=O) |
| HO— | HO— | " | " | CH₃O— | H— | CH₃— |
| HO— | HO— | " | CH₃OCH₂— | CH₃C(=O)—O— | H— | CH₃—C— (C=O) |
| HO— | HO— | " | " | CH₃O— | " | CH₃— |

TABLE IV

| B | B₁ | R″₁ | R″₂ | R″₃ | R″₄ | R″₁₅ |
|---|---|---|---|---|---|---|
| HO— | HO— | H— | CH₃COCH₂— (C=O) | CH₃CO— (C=O) | H— | CH₃C— (C=O) |
| CH₃O— | HO— | " | " | " | " | " |
| C₂H₅O— | HO— | " | " | " | " | " |

TABLE IV-continued

| B | $B_1$ | $R''_1$ | $R''_2$ | $R''_3$ | $R''_4$ | $R''_{15}$ |
|---|---|---|---|---|---|---|
| HS— | HO— | " | " | " | " | " |
| $CH_3S$— | HO— | " | " | " | " | " |
| $C_2H_5S$— | HO— | " | " | " | " | " |
| H— | HO— | " | " | " | " | " |
| HO— | H— | " | " | " | " | " |
| HO— | $CH_3O$— | " | " | " | " | " |
| HO— | HO— | " | $-CH_2Cl$ | " | " | " |
| HO— | HO— | " | $-CH_2Br$ | " | " | " |
| HO— | HS— | " | $CH_3\overset{O}{\overset{\|}{C}}OCH_2-$ | " | " | " |
| HO— | $CH_3S$— | " | " | " | " | " |
| HO— | $C_2H_5S$— | H— | $CH_3\overset{O}{\overset{\|}{C}}OCH_2$ | $CH_3\overset{O}{\overset{\|}{C}}O-$ | H— | $CH_3\overset{O}{\overset{\|}{C}}-$ |
| HO— | HO— | " | $\phi CH_2OCH_2-$ | $\phi CH_2O-$ | H— | $\phi CH_2-$ |
| HO— | HO— | " | $\phi CH_2O-$ | " | " | " |
| HO— | " | " | $CH_3O-$ | $CH_3\overset{O}{\overset{\|}{C}}-O-$ | " | $CH_3\overset{O}{\overset{\|}{C}}-$ |
| HO— | " | " | $C_2H_5-$ | H— | " | " |
| HO— | " | " | $CH_3\overset{O}{\overset{\|}{C}}-OCH_2-$ | $CH_3\overset{O}{\overset{\|}{C}}-O-$ | $CH_3OCH_2-$ | " |
| HO— | " | " | " | " | $C_2H_5-$ | " |
| HO— | " | $CH_3OCH_2-$ | H— | " | H— | " |
| HO— | " | $\phi CH_2OCH_2-$ | " | " | " | $\phi CH_2-$ |
| HO— | " | H— | $-CH_2OC(C_6H_5)_3$ | $CH_3\overset{O}{\overset{\|}{C}}O-$ | " | $CH_3\overset{O}{\overset{\|}{C}}-$ |
| HO— | " | " | " | $-OCH_3$ | " | $CH_3-$ |
| HO— | " | $CH_3\overset{O}{\overset{\|}{C}}-OCH_2-$ | H— | H— | $CH_3\overset{O}{\overset{\|}{C}}O-$ | $CH_3\overset{O}{\overset{\|}{C}}-$ |
| HO— | HO— | $CH_3\overset{O}{\overset{\|}{C}}-OCH_2-$ | H— | $CH_3O-$ | H— | $CH_3-$ |
| HO— | HO— | " | $CH_3OCH_2-$ | $CH_3\overset{O}{\overset{\|}{C}}-O-$ | H— | $CH_3-\overset{O}{\overset{\|}{C}}-$ |
| HO— | HO— | " | " | $CH_3O-$ | " | $CH_3-$ |

Preparation 7

N,N-Dicarbobenzyloxy-4',6'-dihydroxy-3'-(S)-dihydrospectinomycin

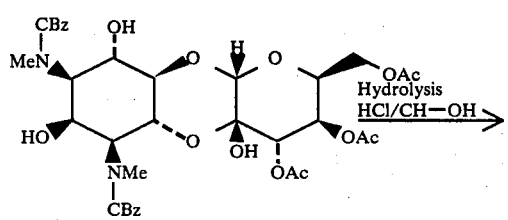

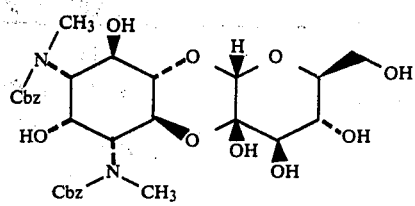

Preparation 8

N,N'-Dicarbobenzyloxy-5'-demethyl-4'-(R)-hydroxy-3'-(R)-dihydrospectinomycin

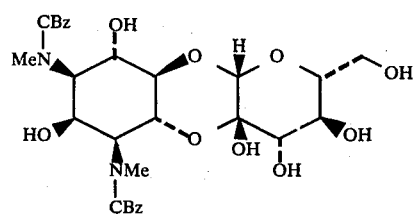

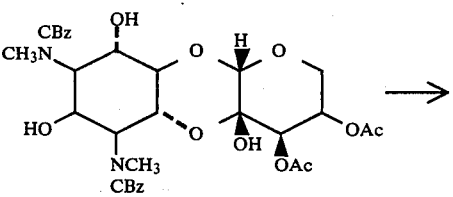

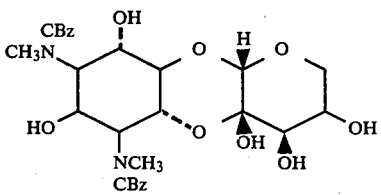

The compound of Preparation 4 (166 mg is dissolved in methanolic hydrogen chloride (5 ml). The methanolic hydrogen chloride is prepared by adding acetyl chloride (0.52 ml) to absolute methanol (15.0 ml). After standing for about 22 hours the solvent is concentrated, diluted with chloroform and a drop of trimethylamine is added and the solution is concentrated again to give a glass (119 mg). CMR (d$_6$—CH$_3$COCH$_3$) 31.8, 57.5, 60.6, 62.4, 65.2, 66.4, 67.3, 68.9, 74.3, 74.9, 77.6, 78.3, 93.1, 96.1, 128.4, 129.2, 138.2, 157.1 (no acetyl signals).

Likewise, using a procedure similar to that used in Preparation 7 but substituting the compound having the formula:

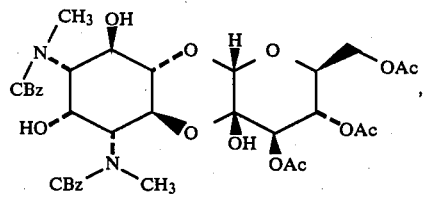

as prepared in Preparation 4a, yields the corresponding deprotected spectinomycin analog having the formula:

Diacetate of Preparation 5 (2.0 g., 2.90 mmol) is dissolved in 50 ml. of anhydrous methanol and 1.0 g. (5.74 mmol) of K$_2$HPO$_4$ is added. The mixture is stirred 2.5 hours at room temperature and filtered; the filtrate being washed with three 5 ml. aliquots of methanol. Solvent is removed in vacuo and the solid, white residue is chromatographed on 75 g. of silica gel (MeOH/CHCl$_3$ gradient) to give 1.25 g. (2.07 mmol, 71%) N,N'-dicarbobenzyloxy-5'-demethyl-4'-hydroxy-3'(R)-dihydrospectinomycin as a white solid: m.p. 139.9°–150°; IR (CHCl$_3$) 3600, 3000, 1680, 1450, 1350, 1150, 1080 cm$^{-1}$; CMR (d$_6$-acetone) δ 158.4, 158.1, 137.8, 129.2, 128.7, 128.5, 94.6, 74.8, 74.3, 68.0, 66.5, 65.4, 64.1, 60.7, 57.7, 31.6; MS (for pentatrimethylsilyl ether) C$_{44}$H$_{76}$N$_2$O$_{12}$Si$_5$ requires 964.42445; found 964.42597.

Using the same procedure as outlined in Preparation 7 or 8, protected "oxy" groups on the sugar moiety are hydrolyzed from corresponding deoximated compounds to obtain the following compounds:

TABLE V

| B | B$_1$ | R$_1$ | R$_2$ | R$_3$ | R$_4$ | R$_{15}$ |
|---|---|---|---|---|---|---|
| HO— | HO— | H— | HOCH$_2$— | HO— | H— | H— |
| CH$_3$O— | " | " | " | " | " | " |
| C$_2$H$_5$O— | " | " | " | " | " | " |
| HS— | " | " | " | " | " | " |
| CH$_3$S— | " | " | " | " | " | " |
| C$_2$H$_5$S— | " | " | " | " | " | " |

TABLE V-continued

[Structure: cyclohexane with N(CH3)(CBz), R6, B, O, linker to pyranose ring with R1, R2, R3, R4, OR15, OH; second N(CH3)(CBz) and B1]

| B | B₁ | R₁ | R₂ | R₃ | R₄ | R₁₅ |
|---|---|---|---|---|---|---|
| H— | " | " | " | " | " | " |
| HO— | H— | " | " | " | " | " |
| " | CH₃O— | " | " | " | " | " |
| " | HO— | " | —CH₂—Cl | " | " | " |
| " | " | " | —CH₂Br | " | " | " |
| " | HS— | " | HOCH₂— | " | " | " |
| " | CH₃S— | " | " | " | " | " |
| " | C₂H₅S— | " | " | " | " | " |
| " | HO— | " | " | " | " | " |
| " | " | " | CH₃O— | " | " | " |
| " | " | " | C₂H₅— | " | " | " |
| " | " | " | HOCH₂— | HO— | CH₃OCH₂— | " |
| " | " | " | " | " | C₂H₅— | " |
| " | " | CH₃OCH₂— | H— | " | H— | " |
| " | " | HOCH₂— | " | " | " | " |
| " | " | H— | —CH₂OH | " | " | " |
| " | " | " | " | —OCH₃ | " | CH₃— |
| " | " | HOCH₂— | " | H— | HO— | H— |
| " | " | " | H— | CH₃O— | H— | CH₃— |
| " | " | " | CH₃OCH₂— | HO— | " | H— |
| " | " | " | " | CH₃O— | " | CH₃— |

TABLE VI

[Structure: cyclohexane with N(CH3)(CBz), R6, B, O, linker to pyranose ring with R1, R2, R3, R4, OR15, OH; second N(CH3)(CBz) and B1; S linkage]

| B | B₁ | R″₁ | R₂ | R″₃ | R₄ | R₁₅ |
|---|---|---|---|---|---|---|
| HO— | HO— | H— | HOCH₂— | HO— | H— | H— |
| CH₃O— | " | " | " | " | " | " |
| C₂H₅O— | " | " | " | " | " | " |
| HS— | " | " | " | " | " | " |
| CH₃S— | " | " | " | " | " | " |
| C₂H₅S— | " | " | " | " | " | " |
| H— | " | " | " | " | " | " |
| HO— | H— | " | " | " | " | " |
| " | CH₃O— | " | " | " | " | " |
| " | HO— | " | —CH₂—Cl | " | " | " |
| " | " | " | —CH₂Br | " | " | " |
| " | HS— | " | HOCH₂— | " | " | " |
| " | CH₃S— | " | " | " | " | " |
| " | C₂H₅S— | " | " | " | " | " |
| " | HO— | " | " | " | " | " |
| " | " | " | CH₃O— | " | " | " |
| " | " | " | C₂H₅— | " | " | " |
| " | " | " | HOCH₂— | HO— | CH₃OCH₂— | " |
| " | " | " | " | " | C₂H₅— | " |
| " | " | CH₃OCH₂— | H— | " | H— | " |
| " | " | HOCH₂— | " | " | " | " |
| " | " | H— | —CH₂OH | H— | " | " |
| " | " | " | " | —OCH₃ | " | CH₃— |
| " | " | HOCH₂— | " | H— | HO— | H— |
| " | " | " | H— | CH₃O— | H— | CH₃— |
| " | " | " | CH₃OCH₂— | HO— | " | H— |
| " | " | " | " | CH₃O— | " | CH₃— |

EXAMPLE 1

4′-(R)-6′-Dihydroxy-3′-(S)dihydrospectinomycin dihydrochloride

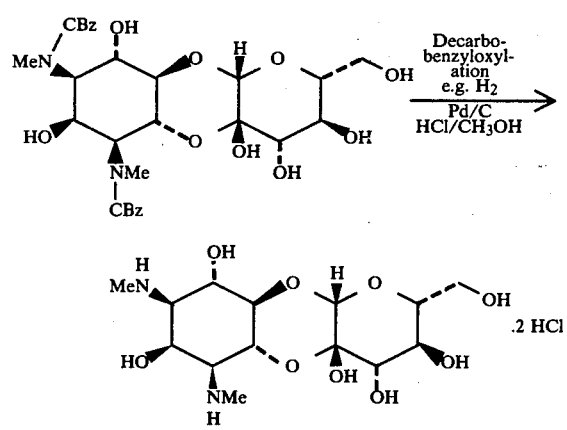

Compound from Preparation 7 (110 mg) is dissolved in absolute methanol (30 ml); 1 N absolute methanolic HCl (0.7 ml) and 10% Pd/C (100 mg) are added. The mixture is agitated under 28 psi of hydrogen for about 30 hours at which time the catalyst is filtered off, washed with methanol and the filtrate was concentrated to 97 mg. Crystallization from methanol gave 35 mg (mp 260°–265° dec.) CMR (D$_2$O, external TMS) 31.5, 32.0, 59.9, 60.8, 61.7, 62.8, 66.3, 67.3, 68.7, 71.5, 77.1, 77.5, 93.5, 95.5.

Again substituting compound having mirror image substituents at C-3′, C-4′ and C-5′ of the reactant in Example 1, a similar hydrogenation procedure unblocks the amine moieties and yields

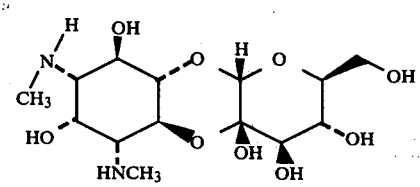

EXAMPLE 2

4′-(R)-hydroxy-5′-demethyl-3′-(R)-dihydrospectinomycin dihydrochloride

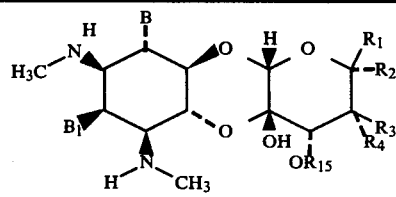

N,N′-Dicarbobenzyloxy-5′-demethyl-4′-hydroxy-3′-(R)-dihydrospectinomycin, (300 mg, 0.50 mmol) is added to a suspension of 750 mg. of 10% PD~ on carbon in 20 ml of absolute ethanol. The mixture is treated with 40 psi of hydrogen in a Parr apparatus 22 hours at room temperature. The catalyst is filtered off and washed with more ethanol, 1.1 ml. (1.10 mmol) of a 1 N HCl in ethanol solution is added and the solution is concentrated in vacuo to give 170 mg (0.42 mmol, 80%) of product as a white solid. Analysis by TLC on silica gel (CHCl$_3$:MeOH:NH$_4$OH/3:4:2) shows one major spot (Rf=0.3) with two minor impurities. CMR analysis shows one predominant product with evidence of impurities: CMR (D$_2$O) δ 94.0, 93.0, 73.5, 71.6, 67.4, 66.6, 66.2, 64.0, 62.9, 61.5, 59.8, 32.3.

Products of the invention are obtained by deblocking amines from corresponding intermediates by using hydrogenation procedures outlined in Examples 1 and 2. Such products are:

TABLE VII

| B | B$_1$ | R$_1$ | R$_2$ | R$_3$ | R$_4$ | R$_{15}$ |
|---|---|---|---|---|---|---|
| HO— | HO— | H— | HOCH$_2$— | HO— | H— | H— |
| CH$_3$O— | " | " | " | " | " | " |
| C$_2$H$_5$O— | " | " | " | " | " | " |
| HS— | " | " | " | " | " | " |
| CH$_3$S— | " | " | " | " | " | " |
| C$_2$H$_5$S— | " | " | " | " | " | " |
| H— | " | " | " | " | " | " |
| HO— | H— | H— | HOCH$_2$— | HO— | H— | H— |
| HO— | CH$_3$O— | H— | HOCH$_2$— | HO— | H— | H— |
| HO— | HO— | " | —CH$_2$—Cl | " | " | " |
| HO— | " | " | —CH$_2$Br | " | " | " |
| HO— | HS— | " | HOCH$_2$— | " | " | " |
| HO— | CH$_3$S— | " | " | " | " | " |
| HO— | C$_2$H$_5$S— | " | " | " | " | " |

TABLE VII-continued

| B | B₁ | R₁ | R₂ | R₃ | R₄ | R₁₅ |
|---|---|---|---|---|---|---|
| HO— | HO— | " | " | " | " | " |
| HO— | HO— | H— | CH₃O— | HO— | H— | H— |
| HO— | " | " | C₂H₅— | H— | " | " |
| HO— | " | " | HOCH₂— | HO— | CH₃OCH₂— | " |
| HO— | " | " | " | " | C₂H₅— | " |
| HO— | " | CH₃OCH₂— | H— | " | H— | " |
| HO— | " | HOCH₂— | " | " | " | " |
| HO— | " | H— | —CH₂OH | " | " | " |
| HO— | " | " | " | —OCH₃ | " | CH₃— |
| HO— | " | HOCH₂— | " | H— | HO— | H— |
| HO— | " | " | H— | CH₃O— | H— | CH₃— |
| HO— | " | " | CH₃OCH₂— | HO— | " | H— |
| HO— | " | " | " | CH₃O— | " | CH₃— |

TABLE VIII

| B | B₁ | R₁ | R₂ | R₃ | R₄ | R₁₅ |
|---|---|---|---|---|---|---|
| HO— | HO— | H— | HOCH₂— | HO— | H— | H— |
| CH₃O— | HO— | H— | HOCH₂— | HO— | H— | H— |
| C₂H₅O— | " | " | " | " | " | " |
| HS— | " | " | " | " | " | " |
| CH₃S— | " | " | " | " | " | " |
| C₂H₅S— | " | " | " | " | " | " |
| H— | HO— | H— | HOCH₂— | HO— | H— | H— |
| HO— | H— | H— | HOCH₂— | HO— | H— | H— |
| HO— | CH₃O— | H— | HOCH₂— | HO— | H— | H— |
| HO— | HO— | " | —CH₂—Cl | " | " | " |
| HO— | " | " | —CH₂Br | " | " | " |
| HO— | HS— | " | HOCH₂— | " | " | " |
| HO— | CH₃S— | " | " | " | " | " |
| HO— | C₂H₅S— | " | " | " | " | " |
| HO— | HO— | " | " | " | " | " |
| HO— | " | " | CH₃O— | HO— | " | " |
| HO— | " | " | C₂H₅— | H— | " | " |
| HO— | " | " | HOCH₂— | HO— | CH₃OCH₂— | " |
| HO— | " | " | " | " | C₂H₅— | " |
| HO— | " | CH₃OCH₂— | H— | " | H— | " |
| HO— | " | HOCH₂— | " | " | " | " |
| HO— | " | H— | —CH₂OH | " | " | " |
| HO— | " | " | " | —OCH₃ | " | CH₃— |
| HO— | " | HOCH₂— | " | H— | HO— | H— |
| HO— | " | " | H— | CH₃O— | H— | CH₃— |
| HO— | " | " | CH₃OCH₂— | HO— | " | H— |
| HO— | " | " | " | CH₃O— | " | CH₃— |

Other compounds having various substituents may be made by utilizing appropriate sugars and appropriate actinamines as starting materials.

I claim:

1. Anomers and asteric mixtures of a compound having the formula

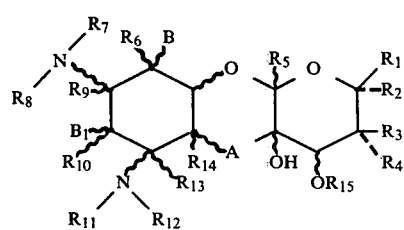

wherein $R_1$ through $R_4$ may be the same or different and are selected from the group consisting of hydrogen, lower alkyl, lower alkenyl, lower alkynyl, lower haloalkyl, lower aminoalkyl, —OX and —$(CH_2)_n$—OX with the proviso that $R_1$ and $R_2$ are not OH and when one of $R_2$ or $R_4$ is OH the other cannot be OX, wherein X is selected from the group consisting of hydrogen, lower alkyl, lower alkenyl, and lower alkynyl, n is an integer of from one to four, $R_5$–$R_{15}$ are selected from the group consisting of hydrogen, lower alkyl, lower alkenyl and lower alkynyl with the proviso that one of $R_7$ and $R_8$ is always hydrogen and one of $R_{11}$ and $R_{12}$ is always hydrogen, A is oxygen or sulfur, B and $B_1$ are selected from the group consisting of hydrogen, hydroxy, lower alkoxy, —O—lower alkenyl, thiol, thio lower alkyl and thio lower alkenyl with the proviso that when the compound is selected from the group consisting of

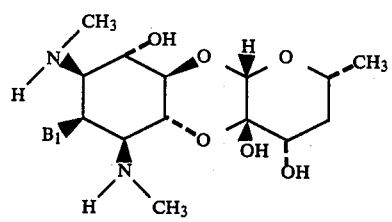

$B_1$ cannot be hydroxy; and when the compound has the formula

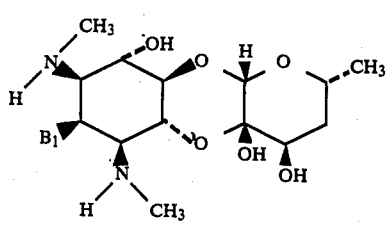

and

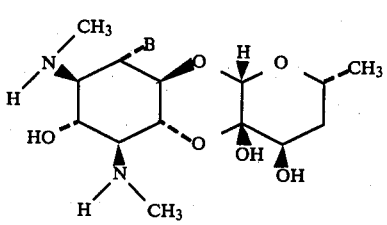

B and $B_1$ cannot be selected from the group consisting of hydrogen and hydroxy, and when the compound has the formula

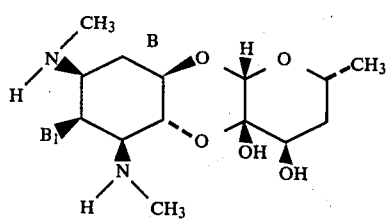

B and $B_1$ cannot both be hydroxy.

2. A compound of claim 1 having the formula

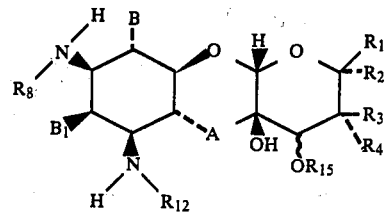

wherein $R_8$ and $R_{12}$ are lower alkyl, B and $B_1$ are hydroxy or lower alkoxy, $R_{15}$ is hydrogen or lower alkyl and $R_1$–$R_4$ are hydrogen, —OX or —$CH_2$OX wherein X is hydrogen; so that $R_1$ and $R_2$ are not OH, and when $R_3$ or $R_4$ is OH, the other cannot be OX.

3. 4'-(R)-6'-Dihydroxy-3'(S)dihydrospectinomycin, a compound according to claim 2.

4. The dihydrochloride salt of the compound of claim 3.

5. 4'-(R)-Hydroxy-5'-demethyl-3'-(R)-dihydrospectinomycin, a compound of claim 2.

6. The dihydrochloride salt of the compound of claim 5.

7. A process for preparing a compound having the formula

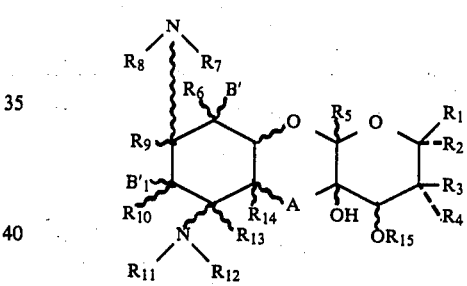

wherein $R_1$ through $R_4$ may be the same or different and are selected from the group consisting of hydrogen, lower alkyl, lower alkenyl, lower alkynyl, lower haloalkyl, lower aminoalkyl, —OX and —$(CH_2)_n$OX with the proviso that $R_1$ and $R_2$ are not OH and when one of $R_3$ or $R_4$ is OH, the other cannot be OX, wherein X is selected from the group consisting of hydrogen, lower alkyl, lower alkenyl, and lower alkynyl, n is an integer of from one to four, $R_5$–$R_{15}$ are selected from the group consisting of hydrogen, lower alkyl, lower alkenyl and lower alkynyl with the proviso that one of $R_7$ and $R_8$ is always hydrogen and one of $R_{11}$ and $R_{12}$ is always hydrogen, A is oxygen or sulfur, B' and $B_1'$ are selected from the group consisting of hydrogen, hydroxy, lower alkoxy, —O—lower alkenyl, thiol, thio lower alkyl and thio lower alkenyl, which comprises Step (1) Reaction of a compound having the formula

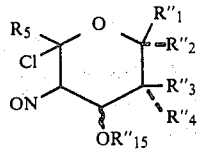

with a compound having the formula

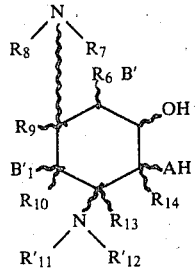

to prepare a compound having the formula

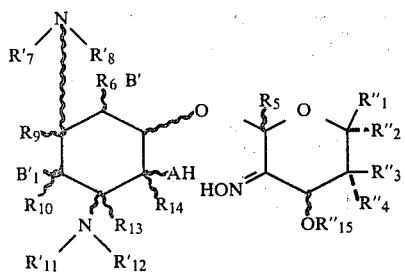

wherein $R_1''$ through $R_4''$ may be the same or different and are selected from the group consisting of hydrogen, lower alkyl, lower alkenyl, lower alkynyl, lower haloalkyl, lower aminoalkyl, —OX" and —(CH$_2$)—OX", wherein X" is selected from the group consisting of lower alkyl, lower alkenyl, lower alkynyl, acyl and aralkyl, $R_7'$, $R_8'$, $R_{11}'$ and $R_{12}'$ are selected from the group consisting of lower alkyl, lower alkenyl, lower alkynyl and a blocking group selected from the group consisting of acyl, aralkoxycarbonyl, aryloxy carbonyl, halogenated alkoxy carbonyl and alkyloxycarbonyl with the proviso that one of $R_7'$ and $R_8'$ is always a blocking group and one of $R_{11}'$ and $R_{12}'$ is always a blocking group and $R_{15}''$ is lower alkyl, lower alkenyl, lower alkynyl, acyl or aralkyl, Step (2) Deoximation of compound IV of step 1 to prepare a compound having the formula

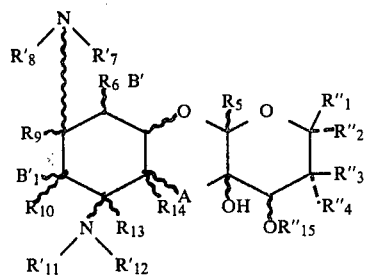

Step (3) Deprotection of Compound V of Step 2 to a compound of formula I.

8. A process according to claim 7 for preparing a compound having the formula

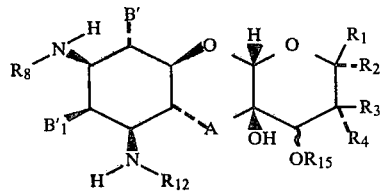

wherein $R_8$ and $R_{12}$ are lower alkyl, B' and $B_1'$ are hydroxy or lower alkoxy, $R_{15}$ is hydrogen or lower alkyl, and $R_1$ through $R_4$ are hydrogen, —OX or —CH$_2$OX with the proviso that $R_1$ and $R_2$ are not OH and when one of $R_3$ or $R_4$ is OH, the other cannot be OX, wherein X is hydrogen which comprises:

Step (1) Reaction of a compound having the formula

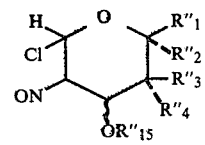

with a compound having the formula

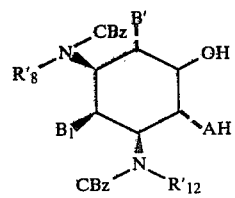

to prepare a compound having the formula

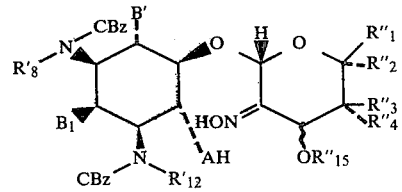

wherein CBz is carbobenzyloxy, $R_8'$ and $R_{12}'$ are lower alkyl, $R_{15}''$ is acyl or lower alkyl, $R_1''$ through $R_4''$ are hydrogen, —OX" or —CH$_2$OX"

wherein X'' is acyl and B and B₁ hydroxy or lower alkoxy;

Step (2) Deoximation of a compound of step I to prepare a compound having the formula

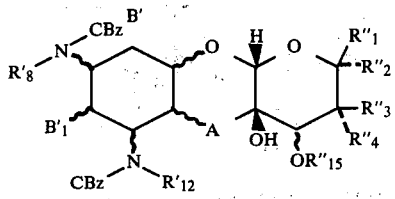

Step (3) Deprotection of a compound of step 2 to the compound of Formula Ia.

9. A process according to claim 8 for preparing a compound such that the compound prepared in Step (1) is selected from the group consisting of 5-O-(3',4'-Di-O-acetyl-2'-deoxy-2'-oximino-D-arabinopyranosyl)-N,N'-dicarbobenzyloxyactinamine, 5-O-(3',4',6'-tri-O-acetyl-2'-oximino-2'-deoxy-β-D-glucopyranosyl)-N,N'-dicarbobenzyloxyactinamine, and 5-O-(4',6'-Di-O-acetyl-3'-O-methyl-2'-oximino-2'-deoxy-β-D-glucopyranosyl)-N,N'-dicarbobenzyloxy actinamine.

10. Process according to claim 8 for preparing a compound such that the compound prepared in Step (2) is selected from the group consisting of N,N'-dicarbobenzyloxy-3'-O-acetyl-4'-(R)-acetoxy-5'-demethyl-3'-(R)-dihydrospectinomycin, N,N'-dicarbobenzyloxy-3'-O-methyl-4'-(R)-acetoxy-6'-acetoxy-3'-(S)-dihydrospectinomycin, N,N'-dicarbobenzyloxy-3'-O-acetyl-4'-(R)-acetoxy-6'-acetoxy-3'-(S)-dihydrospectinomycin.

11. Process according to claim 8 for preparing a compound selected from the group consisting of 4'-(R)-hydroxy-5'-demethyl-3'-(R)-dihydrospectinomycin, 4'-(R)-hydroxy-6'-hydroxy-3'-(S)-dihydrospectinomycin.

12. A process for preparing a compound having the formula

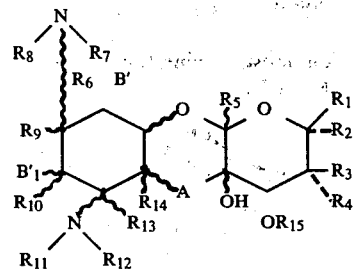

wherein R₁ through R₄ may be the same or different and are selected from the group consisting of hydrogen, lower alkyl, lower alkenyl, lower alkynyl, lower haloalkyl, lower aminoalkyl, —OX and —(CH₂)ₙ—OX, with the proviso that R₁ and R₂ are not OH and when one of R₃ or R₄ is OH, the other cannot be OX, wherein X is selected from the group consisting of hydrogen, lower alkyl, lower alkenyl, and lower alkynyl, n is an integer of from one to four, R₅–R₁₅ are selected from the group consisting of hydrogen, lower alkyl, lower alkenyl and lower alkynyl, with the proviso that one of R₇ and R₈ is always hydrogen and one of R₁₁ and R₁₂ is always hydrogen, A is selected from the group consisting of oxygen and sulfur, B' and B₁' are selected from the group consisting of hydrogen, hydroxy, lower alkoxy, -O-lower alkenyl, thiol, thio lower alkyl and thio lower alkenyl, which comprises deblocking the amine groups on the actinamine moiety of compounds having the formula

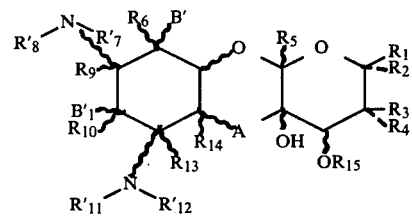

wherein R₇', R₈', R₁₁' and R₁₂' are selected from the group consisting of lower alkyl, lower alkenyl, lower alkynyl and a blocking group selected from the group consisting of acyl, aralkoxy carbonyl, aryloxy carbonyl, halogenated alkoxycarbonyl and alkyloxycarbonyl with the proviso that one of R₇' and R₈' is always a blocking group and one of R₁₁' and R₁₂' is always a blocking group.

13. A process according to claim 12 for preparing a compound having the formula

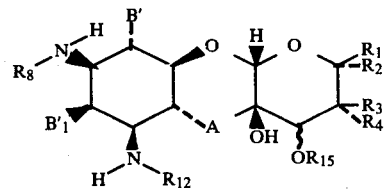

which comprises deblocking the amine group on the actinamine moiety of compounds selected from the group consisting of

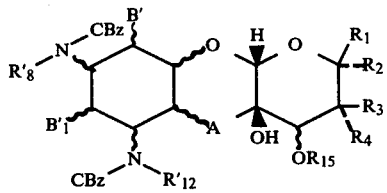

thereto, wherein CBz is carbobenzyloxy, R₈, R₈', R₁₂ and R₁₂' are lower alkyl, B' and B₁' are hydroxy or lower alkoxy, R₁₅ is hydrogen or lower alkyl and R₁ through R₄ are hydrogen, —OX or —CH₂OX wherein X is hydrogen with the proviso that R₁ and R₂ are not OH and when R₃ or R₄ is OH, the other cannot be OX.

14. A process according to claim 13 wherein R₁, R₂, R₄ and R₁₅ are hydrogen and R₃ is hydroxy so that the anomer prepared is 4'-(R)-hydroxy-5'-demethyl-3'-(R)-dihydrospectinomycin.

15. A process according to claim 13 wherein R₂ is —CH₂OH, R₃ is hydroxy, R₁, R₄ and R₁₅ are hydrogen in structure I so that the anomer prepared is 4'-(R)-hydroxy-6'-hydroxy-3'(S)-dihydrospectinomycin.

16. Anomers and asteric mixtures of a compound having the formula

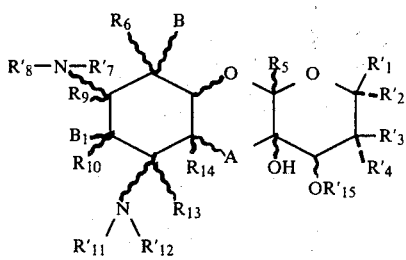

V or Va wherein $R_1'$ through $R_4'$ may be the same or different and are selected from the group consisting of hydrogen, lower alkyl, lower alkenyl, lower alkynyl, lower haloalkyl, lower aminoalkyl, —OX' and —(CH$_2$)$_n$—OX' with the proviso that $R_1$ and $R_2$ are not OH and when one of $R_3$ or $R_4$ is OH, the other cannot be OX', wherein X' is selected from the group consisting of hydrogen, lower alkyl, lower alkenyl, lower alkynyl, acyl and aralkyl, n is an integer of from one to four, $R_5$-$R_6$, $R_9$-$R_{10}$, $R_{13}$ and $R_{14}$ are selected from the group consisting of hydrogen, lower alkyl, lower alkenyl and lower alkynyl, $R_{15}'$ is selected from the group consisting of hydrogen, lower alkyl, lower alkenyl, lower alkynyl, acyl and aralkyl, A is oxygen or sulfur, $R_7'$, $R_8'$, $R_{11}'$ and $R_{12}'$ are selected from the group consisting of lower alkyl, lower alkenyl, lower alkynyl and a blocking group selected from the group consisting of aralkoxy carbonyl, aryloxy carbonyl, halogenated alkoxycarbonyl and alkyloxy carbonyl with the proviso that one of $R_7'$ and $R_8'$ and one of $R_{11}'$ and $R_{12}'$ is always a blocking group, B and B$_1$ are selected from the group consisting of hydrogen, hydroxy, lower alkoxy, -O-lower alkenyl, thiol, thio lower alkyl and thio lower alkenyl with the proviso that when the compound is selected from the group consisting of compounds having the formula

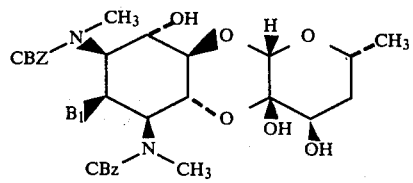

B$_1$ cannot be hydroxy; and when the compound has the formula

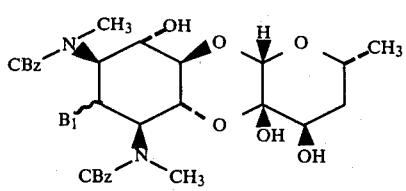

and

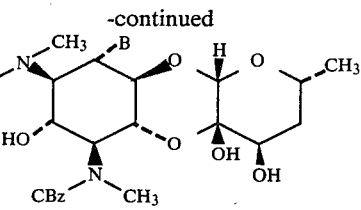

B and B$_1$ cannot be selected from the group consisting of hydrogen and hydroxy, and when the compound has the formula

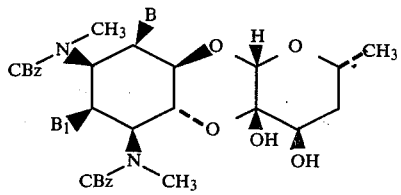

B and B$_1$ cannot both be hydroxy.

17. A compound of claim 16 having the formula

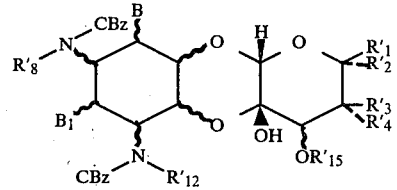

wherein CBz is carbobenzyloxy, $R_8'$ and $R_{12}'$ are lower alkyl, B and B$_1$ are hydroxy or lower alkoxy, $R_{15}'$ is hydrogen or lower alkyl, and $R_1'$-$R_4'$ are hydrogen, —OX' or —CH$_2$OX' wherein X' is hydrogen with the proviso that $R_1'$ and $R_2'$ are not OH and when one of $R_3'$ or $R_4'$ is OH, the other cannot be OX'.

18. N,N'-Dicarbobenzyloxy-4',6'-dihydroxy-3'(S)-dihydrospectinomycin, a compound according to claim 17.

19. N,N'-Dicarbobenzyloxy-4'-(R)-hydroxy-5'-demethyl-3'-(R)-dihydrospectinomycin, a compound according to claim 17.

20. A compound of claim 16 having the formula

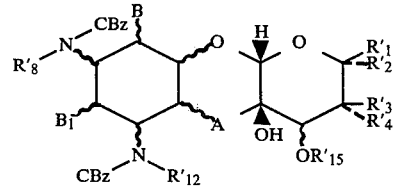

wherein CBz is carbobenzyloxy, $R_8'$ and $R_{12}'$ are lower alkyl, B and B$_1$ are hydroxy or lower alkoxy, $R_{15}'$ is lower alkyl or acyl and $R_1'$-$R_4'$ are hydrogen, —OX' or —CH$_2$OX' wherein X' is acyl.

21. N,N'-Dicarbobenzyloxy-3'-O-acetyl-4'-(R)-6'-diacetoxy-3'-(S)-dihydrospectinomycin, a compound according to claim 20.

22. N,N'-dicarbobenzyloxy-3'-O-acetyl-4'-(R)-acetoxy-5'-demethyl-3'-(R)-dihydrospectinomycin, a compound according to claim 20.

23. N,N'-dicarbobenzyloxy-3'-O-methyl-4'-(R)-acetoxy-6'-acetoxy-3'-(S)-dihydrospectinomycin, a compound according to claim 20.

24. A process for preparing a compound having the formula

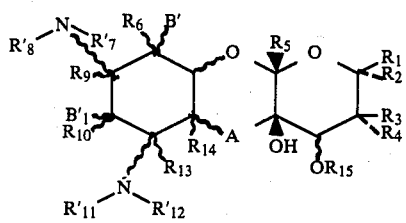
Va wherein $R_1$ through $R_4$ may be the same or different and are selected from the group consisting of hydrogen, lower alkyl, lower alkenyl, lower alkynyl, lower haloalkyl, lower aminoalkyl, —OX and —$(CH_2)_n$—OX, with the proviso that $R_1$ and $R_2$ are not OH and when one of $R_3$ and $R_4$ are OH, the other cannot be OX, wherein X is selected from the group consisting of hydrogen, lower alkyl, lower alkenyl and lower alkynyl, n is an integer of from one to four, $R_5$–$R_{15}$ are selected from the group consisting of hydrogen, lower alkyl, lower alkenyl and lower alkynyl, $R_7'$, $R_8'$, $R_{11}'$ and $R_{12}'$ are selected from the group consisting of lower alkyl, lower alkenyl, lower alkynyl and a blocking group selected from the group consisting of aralkoxy carbonyl, aryloxy carbonyl, halogenated alkoxy carbonyl and alkyloxycarbonyl with the proviso that one of $R_7'$ and $R_8'$ is always a blocking group and one of $R_{11}'$ and $R_{12}'$ is always a blocking group, B' and $B_1'$ are selected from the group consisting of hydrogen, hydroxy, lower alkoxy, -o-lower alkenyl, thiol, thio-lower alkyl and thio-lower alkenyl, A is oxygen or sulfur, which comprises removing protective groups in $R_1''$ through $R_4''$ and $R_{15}''$ positions in from a compound having the formula consisting of

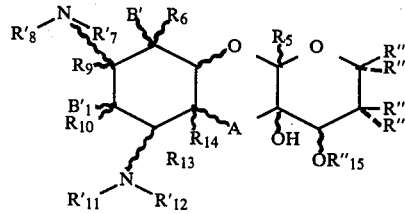
V wherein $R_1''$–$R_4''$ may be the same or different and are selected from the group consisting of hydrogen, lower alkyl, lower alkenyl, lower alkynyl, lower haloalkyl, lower aminoalkyl, —OX'' and —$(CH_2)OX''$, wherein X'' is lower alkyl, lower alkenyl and lower alkynyl, acyl or aralkyl and $R_{15}''$ is lower alkyl, lower alkenyl, lower alkynyl, acyl or aralkyl, with the proviso that at least one of $R_1''$ through $R_4''$ or $R_{15}''$ includes an acyl or aralkyl.

25. A process according to claim 24 for preparing a compound having the formula

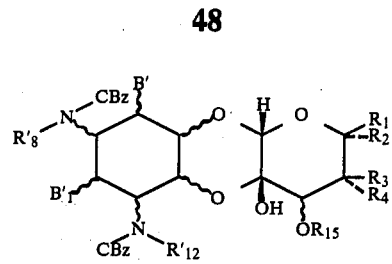

which comprises removing protective groups from the $R_1''$ through $R_4''$ and $R_{15}''$ positions from a compound having the formula

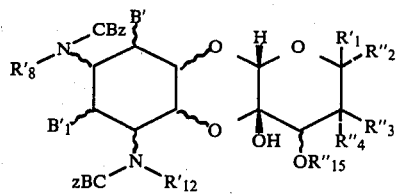

thereto, wherein CBz is carbobenzyloxy, $R_8'$ and $R_{12}'$ are lower alkyl, B' and $B_1'$ are hydroxy or lower alkoxy, $R_{15}$ is hydrogen or lower alkyl, $R_{15}''$ is acyl or lower alkyl, $R_1$ through $R_4$ are hydrogen, —OX or —$CH_2OX$ wherein X is hydrogen and $R_1''$ through $R_4''$ are hydrogen, —OX'' or —$CH_2OX''$ wherein X'' is acyl.

26. A process according to claim 25 wherein $R_1$, $R_2$, $R_4$, $R_{15}$ are hydrogen, and $R_3$ is hydroxy such that the compound prepared is N,N'-dicarbobenzyloxy-4'-(R)-hydroxy-5'-demethyl-3'-(R)-dihydrospectinomycin.

27. A process according to claim 25 wherein $R_1$, $R_4$ and $R_{15}$ are hydrogen, $R_2$ is —$CH_2OH$, and $R_3$ is hydroxy such that the compound prepared is N,N'-dicarbobenzyloxy-4',6'-dihydroxy-3'-(S)-dihydrospectinomycin.

28. A process for preparing a compound having the formula

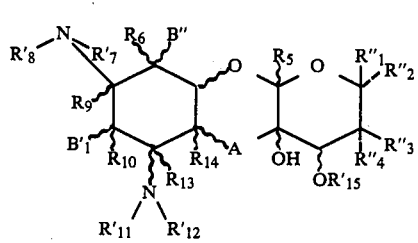
V wherein $R_1''$–$R_4''$ are selected from the group consisting of hydrogen, lower alkyl, lower alkenyl, lower alkynyl, lower haloalkyl, lower aminoalkyl, —OX'' and —$(CH_2)_nOX''$;

wherein X'' is selected from the group consisting of lower alkyl, lower alkenyl, lower alkynyl, acyl and aralkyl;

n is an integer of from one to four;

$R_{15}''$ is acyl, aralkyl, lower alkyl, lower alkenyl, lower alkynyl;

$R_5$–$R_6$, $R_9$–$R_{10}$, $R_{13}$–$R_{14}$ are selected from the group consisting of hydrogen, lower alkyl, lower alkenyl and lower alkynyl, $R_7'$, $R_8'$, $R_{11}'$ and $R_{12}'$ are selected from the group consisting of lower alkyl, lower alkenyl, lower alkynyl and a blocking group selected from the group consisting of aralkoxy carbonyl, aryloxy carbonyl, halogenated alkoxy carbonyl and alkyloxycarbonyl with the proviso that one of R₇' and R₈' is always a blocking group and one of R₁₁' and R₁₂' is always a blocking group;

B' and B₁' are selected from the group consisting of hydrogen, hydroxy, lower alkoxy, —o—lower alkenyl, thiol, thio lower alkyl, thio lower alkenyl; and A is oxygen or sulfur, which comprises deoximating a compound having the formula

[Formula IV with substituents R'₈, N, R'₇, R₆, B'', O, R₅, O, R''₁, R''₂, R₉, B'₁, R₁₀, R₁₄, A, N, H, O, H, R''₃, R''₄, OR''₁₅, N, R₁₃, R'₁₁, R'₁₂]

thereto.

29. A process according to claim 28 for preparing a compound having the formula

[Formula with substituents R'₈, N, CBz, B', O, H, O, R''₁, R''₂, B'₁, A, OH, R''₃, R''₄, OR''₁₅, N, CBz, R'₁₂]

which comprises deoximating a compound having the formula

[Formula with substituents R'₈, N, CBz, B', O, H, O, R''₁, R''₂, B'₁, A, HON, H, R''₃, R''₄, OR''₁₅, N, CBz, R'₁₂]

thereto, wherein CBz is carbobenzyloxy, R₈' and R₁₂' are lower alkyl, B' and B₁' are hydroxy or lower alkoxy, R₁₅'' is lower alkyl or acyl, R₁''–R₄'' are hydrogen, —OX'' or —CH₂OX'' wherein X'' is acyl.

30. A process according to claim 29 wherein R₁'', R₂'' and R₄'' are hydrogen, R₃'' is acetyloxy, R₁₅'' is acetyl such that the compound prepared is N,N'-dicarbobenzyloxy-3'-O-acetyl-4'-(R)-acetoxy-5'-demethyl-3'-(R)-dihydrospectinomycin.

31. A process according to claim 29 wherein R₁'' and R₄'' are hydrogen, R₂'' is acetyloxy methyl, R₃'' is acetyloxy, R₁₅'' is acetyl such that the compound prepared is N,N'-dicarbobenzyloxy-3'-O-acetyl-4'-(R)-acetoxy-6'-acetoxy-3'-(S)-dihydrospectinomycin.

32. A process according to claim 29 wherein R₁'' and R₄'' are hydrogen, R₂'' is acetyloxymethyl and R₃' is acetyloxy, R₁₅'' is methyl such that the compound prepared is N,N'-dicarbobenzyloxy-3'-O-methyl-4'-(R)-acetoxy-6'-acetoxy-3'-(S)-dihydrospectinomycin.

33. Anomers and asteric mixtures of a compound having the formula

[Formula IV with substituents R'₈, N, R'₇, R₆, B, O, R₅, O, R''₁, R''₂, R₉, B'₁, R₁₀, R₁₄, AH, HON, R''₃, R''₄, OR''₁₅, N, R₁₃, R'₁₁, R'₁₂]

wherein R₁'' through R₄'' may be the same or different and are selected from the group consisting of hydrogen, lower alkyl, lower alkenyl, lower alkynyl, lower haloalkyl, lower aminoalkyl, —OX'' and —(CH₂)ₙ—OX'', wherein X'' is selected from the group consisting of lower alkyl, lower alkenyl, lower alkynyl, acyl and aralkyl, n is an integer of from one to four, R₅–R₆, R₉–R₁₀, R₁₃ and R₁₄ are selected from the group consisting of hydrogen, lower alkyl, lower alkenyl and lower alkynyl, R₁₅'' is lower alkyl, lower alkenyl, lower alkynyl, acyl and aralkyl, A is oxygen or sulfur, R₇', R₈', R₁₁' and R₁₂' are selected from the group consisting of lower alkyl, lower alkenyl, lower alkynyl and a blocking group selected from the group consisting of aralkoxy carbonyl, aryloxy carbonyl, halogenated alkoxy carbonyl and alkyloxy carbonyl with the proviso that one of R₇' and R₈' and one of R₁₁' and R₁₂' is always a blocking group, B and B₁ are selected from the group consisting of hydrogen, hydroxy, lower alkoxy, —O—lower alkenyl, thiol, thio lower alkyl and thio lower alkenyl with the proviso that when the compound is a compound having the formula

[Formula with substituents H, N, CBz, OH, O, H, O, OAc, B'₁, HON, AH, OAc, CBz, N, H, OAc]

wherein CBz is carbobenzyloxy then B₁ cannot be hydrogen.

34. A compound according to claim 33 having the formula

[Formula with substituents R'₈, N, CBz, B, O, H, O, R''₁, R''₂, B₁, HON, AH, R''₃, R''₄, OR''₁₅, CBz, N, R'₁₂]

wherein CBz is carbobenzyloxy, R₈' and R₁₂' are lower alkyl, B and B₁ are hydroxy or lower alkoxy, R₁₅'' is lower alkyl or acyl and R₁''–R₄'' are hydrogen, —OX'' or —CH₂OX'' wherein X'' is acyl.

35. 5-O-(3',4'-di-O-acetyl-2'-deoxy-2'-oximino-D-arabinopyranosyl)-N,N'-dicarbobenzyloxyactinamine, a compound according to claim 34.

36. 5-O-(3',4',6'-tri-O-acetyl-2'-oximino-2'-deoxy-β-D-glucopyranosyl)-N,N'-dicarbobenzyloxyactinamine, a compound according to claim 34.

37. 5-O-(4',6'-di-O-acetyl-3'-O-methyl-2'-oximino-2'-deoxy-β-D-glucopyranosyl)-N,N'-dicarbobenzyloxyactinamine, a compound according to claim 34.

38. A process for preparing a compound having the formula

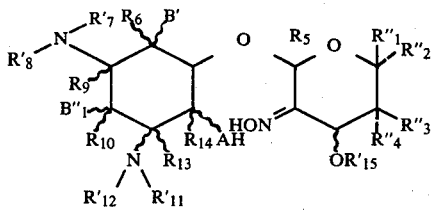   IV which comprises coupling a compound having the formula

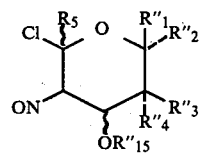   II with a compound having the formula

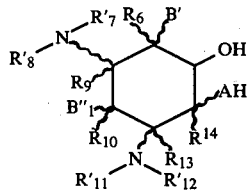   III wherein $R_1''$-$R_4''$ may be the same or different and are selected from the group consisting of hydrogen, lower alkyl, lower alkenyl, lower alkynyl, lower haloalkyl, lower aminoalkyl, —OX" and —$(CH_2)_nOX$";
   wherein X" is selected from the group consisting of lower alkyl, lower alkenyl, lower alkynyl acyl and aralkyl,
   n is an integer of from one to four;
$R_5$-$R_6$, $R_9$-$R_{10}$, $R_{13}$-$R_{14}$ are selected from the group consisting of hydrogen, lower alkyl, lower alkenyl and lower alkynyl,
$R_{15}''$ is acyl, aralkyl, lower alkyl, lower alkenyl and lower alkynyl,
$R_7'$, $R_8'$, $R_{11}'$ and $R_{12}'$ are selected from the group consisting of lower alkyl, lower alkenyl, lower alkynyl and a blocking group selected from the group consisting of aralkoxycarbonyl, aryloxy carbonyl, halogenated alkoxy carbonyl and alkyloxycarbonyl with the proviso that one of $R_7'$ and $R_8'$ is always a blocking group and one of $R_{11}'$ and $R_{12}'$ is always a blocking group;
B' and $B_1''$ are selected from the group consisting of hydrogen, hydroxy, lower alkoxy, —O—lower alkenyl, thiol, thio lower alkyl and thio lower alkenyl; and
A is oxygen or sulfur,
with the proviso that where the prepared compound IV has the formula

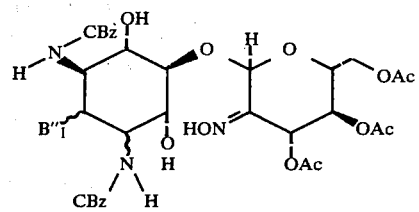

wherein CBz is carbobenzyloxy, then $B_1''$ cannot be hydrogen.

39. A process according to claim 38 wherein the compound made has the formula

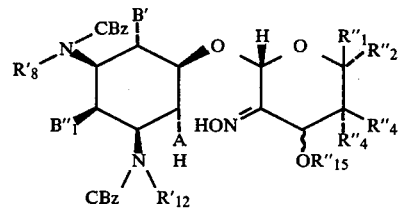

which comprises reacting activated sugars having the formula

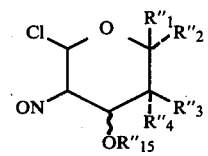

with a protected actinamine having the formula

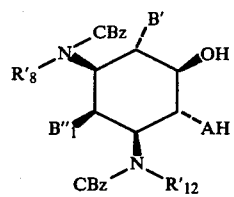

wherein CBz is carbobenzyloxy, $R_8'$ and $R_{12}'$ are lower alkyl, B' and $B_1''$ are hydroxy or lower alkoxy, $R_{15}''$ is lower alkyl or acyl, $R_1''$-$R_4''$ are hydrogen, —OX"', —$CH_2OX$" wherein X" is acyl.

40. A process according to claim 39 wherein $R_1''$, $R_2''$ and $R_4''$ are hydrogen, $R_3''$ is acetyloxy, $R_{15}''$ is acetyl, and B and $B_1$ are hydroxy such that the compound is 5-O-(3',4'-di-O-acetyl-2'-deoxy-2'-oximino-D-arabinopyranosyl)-N,N'-dicarbobenzyloxyactinamine.

41. A process according to claim 39 wherein $R_1''$ and $R_4''$ are hydrogen, $R_2''$ is acetyloxymethyl, $R_3''$ is acetyloxy, $R_{15}''$ is acetyl, and B' and $B_1''$ is hydroxy, such that the compound is 5-O-(3',4',6'-tri-O-acetyl-2'-oximino-2'-deoxy-β-D-glucopyranosyl)-N,N'-dicarbobenzyloxyactinamine.

42. A process according to claim 39 wherein $B_1$, B", $R_1''$ and $R_4''$ are hydrogen, $R_2''$ is acetyloxymethyl, $R_3''$ is acetyloxy and $R_{15}''$ is methyl such that the compound is 5-O-(4',6'-di-O-acetyl-3'-O-methyl-2'-oximino-2'-deoxy-β-D-glucopyranosyl-N,N'-dicarbobenzyloxyactinamine.

* * * * *